United States Patent
Ballance et al.

(10) Patent No.: US 6,290,953 B1
(45) Date of Patent: Sep. 18, 2001

(54) MODULATION OF CELLULAR PROLIFERATION WITH THYMIDINE PHOSPHORYLASE

(75) Inventors: David J. Ballance, Attenborough (GB); Michael G. Courtney, Achenheim (FR); Christopher J. A. Finnis, Lenton; Darrell Sleep, West Bridgford, both of (GB)

(73) Assignee: Delta Biotechnology Ltd., Nottingham (GB)

( * ) Notice: Subject to any disclaimer, the term of this patent is extended or adjusted under 35 U.S.C. 154(b) by 0 days.

(21) Appl. No.: 08/584,760

(22) Filed: Jan. 11, 1996

Related U.S. Application Data

(63) Continuation of application No. 08/211,860, filed as application No. PCT/GB92/01887 on Oct. 15, 1992, now abandoned.

(30) Foreign Application Priority Data

Oct. 15, 1991 (GB) .................................................. 9121815

(51) Int. Cl.[7] .................................................. H01J 19/82
(52) U.S. Cl. ........................................ 424/94.5; 424/178.1
(58) Field of Search ................................ 424/94.5, 178.1

(56) References Cited

U.S. PATENT DOCUMENTS

| | | | |
|---|---|---|---|
| 4,178,212 | * 12/1979 | Krenitsky et al. | 435/32 |
| 4,347,315 | 8/1982 | Krenitsky et al. . | |
| 5,227,302 | * 7/1993 | Heldin et al. | 435/240.2 |
| 5,314,995 | * 5/1994 | Fell et al. | 530/351 |
| 5,756,686 | 5/1998 | Heldin et al. . | |

FOREIGN PATENT DOCUMENTS 0 289 229  11/1988  (EP) .

OTHER PUBLICATIONS

Callard et al., The Cytokine Fact Book, Academic Press Limited, pp. 119, 122, 123 and 133, 1994.*
Yoshimura, A. et al. (1990) "Purification and tissue distribution of human thymidine phosphorylase; high in lymphocytes, reticulocytes and tumors" Biochim. Biophys. Acta. 1034(1):107–113, Apr. 1990.*
Usuki, K. et al. (1992) "Platelet–derived endothelial cell growth factor has thymidine phosphorylase activity" Biochem. Biophys. Res. Comm. 184(3):1311–1316, May 1992.*
Hammerberg, C. et al. (1991) "Elevated thymidine phosphorylase activity in psoriatic lesions accounts for the apparent presence of an epidermal 'growth inhibitor,' but is not itself growth inhibitory" J. Invest. Dermatol. 97:286–290, Aug. 1991.*

* cited by examiner

Primary Examiner—Robert A. Wax
(74) Attorney, Agent, or Firm—Naomi S. Biswas

(57) ABSTRACT

A method of modulating cellular proliferation by the application of a thymidine phosphorylase to an organism. In a further aspect of the subject method, the thymidine phosphorylase is a conjugate which includes a targeting portion adapted to target the conjugate to a specific cell type or anatomical location. The thymidine phosphorylase has a thymidine phosphorylase activity of at least about 5%, preferably at least about 50% and, most preferably, at least about 90%, of the native *E. coli* enzyme.

12 Claims, 22 Drawing Sheets

```
  1 LEU PHE LEU ALA GLN GLU ILE ILE ARG LYS LYS ARG  12
 13 ASP GLY HIS ALA LEU SER ASP GLU GLU ILE ARP PHE  24
 25 PHE ILE ASN GLY ILE ARG ASP ASN THR TLE SER GLU  36
 37 GLY GLN ILE ALA ALA LEU ARG MET THR ILE PHE PHE  48
 49 HIS ASP MET THR MET PRO GLU ARG VAL SER LEU THR  60
     -   -   -   -   ,   -   -   -   -   +   -   -
 61 MET ALA MET ARG ASP SER GLY THR VAL LEU ASP TRP  72
 73 LYS SER LEU HIS LEU ASN GLY PRO ILE VAL ASP LYS  84
 85 HIS SER THR GLY GLY VAL GLY ASP VAL THR SER LEU  96
 97 MET LEU GLY PRO MET VAL ALA ALA CYS GLY GLY TYR 108
109 ILE PRO MET ILE SER GLY ARG GLY LEU GLY HIS THR 120
     -   -   -   -   ,   -   -   -   -   +   -   -
121 GLY GLY THR LEU ASP LYS LEU GLU SER ILE PRO GLY 132
133 PHE ASP ILE PHE PRO ASP ASP ASN ARG PHE ARG GLU 144
145 ILE ILE LYS ASP VAL GLY VAL ALA ILE ILE GLY GLN 156
157 THR SER SER LEU ALA PRO ALA ASP LYS ARG PHE TYR 168
169 ALA THR ARG ASP ILE THR ALA THR VAL ASP SER ILE 180
     -   -   -   -   ,   -   -   -   -   +   -   -
181 PRO LEU ILE THR ALA SER ILE LEU ALA LYS LYS LEU 192
193 ALA GLU GLY LEU ASP ALA LEU VAL MET ASP VAL LYS 204
205 VAL GLY SER GLY ALA PHE MET PRO THR TYR GLU LEU 216
217 SER GLU ALA LEU ALA GLU ALA ILE VAL GLY VAL ALA 216
109 ILE PRO MET ILE SER GLY ARG GLY LEU GLY HIS THR 120
229 ASN GLY ALA GLY VAL ARG THR THR ALA LEU LEU THR 240
     -   -   -   -   ,   -   -   -   -   +   -   -
241 ASP MET ASN GLN VAL LEU ALA SER SER ALA GLY ASN 252
253 ALA VAL GLU VAL ARG GLU ALA VAL GLN PHE LEU THR 264
265 GLY GLU TYR ARG ASN PRO ARG LEU PHE ASP VAL THR 276
277 MET ALA LEU CYS VAL GLU MET LEU ILE SER GLY LYS 288
289 LEU ALA LYS ASP ASP ALA GLU ALA ARG ALA LYS LEU 300
     -   -   -   -   ,   -   -   -   -   +   -   -
301 GLN ALA VAL LEU ASP ASN GLY LYS ALA ALA GLU VAL 312
313 PHE GLY ARG MET VAL ALA ALA GLN LYS GLY PRO THR 324
325 ASP PHE VAL GLU ASN TYR ALA LYS TYR LEU PRO THR 336
337 ALA MET LEU THR LYS ALA VAL TYR ALA ASP THR GLU 348
349 GLY PHE VAL SER GLU MET ASP THR ARG ALA LEU GLY 360
     -   -   -   -   ,   -   -   -   -   +   -   -
361 MET ALA VAL VAL ALA MET GLY GLY GLY ARG ARG GLN 372
373 ALA SER ASP THR ILE ASP TYR SER VAL GLY PHE THR 384
385 ASP MET ALA ARG LEU GLY ASP GLN VAL ASP GLY GLN 396
397 ARG PRO LEU ALA VAL ILE HIS ALA LYS ASP GLU ASN 408
409 ASN TRP GLN GLU ALA ALA LYS ALA VAL LYS ALA ALA 420
     -   -   -   -   ,   -   -   -   -   +   -   -
421 ILE LYS LEU ALA ASP LYS ALA PRO GLU SER THR PRO 432
433 THR VAL TYR ARG ARG ILE SER GLU                 440
```

FIG. 1

OLIGO 1
CTTAGCTCAA GAAATTATTA GAAAAAAAAG AGATGGTCAT GCTTTATCTG ATGAAGAAAT TAGATTCTTC A

OLIGO 2
TTAACGGTAT TAGAGATAAC ACTATTTCTG AAGGTCAAAT TGCTGCTTTA GCTATGACTA TTTCTTCCA T

OLIGO 3
GATATGACTA TGCCAGAAAG AGTTTCTTTA ACTATGGCTA TGAGAGATTC TGGTACTGTT TTAGATTGGA

OLIGO 4
AATCTTTACA TTTAAACGGT CCAATTG

OLIGO 5
TCGACAATTG GACCGTTTAA ATGTAAAGAT TTCCAATCTA AA

OLIGO 6
ACAGTACCAG AATCTCTCAT AGCCATAGTT AAAGAAACTC TTTCTGGCAT AGTCATATCA TGGAAGAAAA

OLIGO 7
TAGTCATAGC TAAAGCAGCA ATTTGACCTT CAGAAATAGT GTTATCTCTA ATACCGTTAA TGAAGAATCT

OLIGO 8
AATTTCTTCA TCAGATAAAG CATGACCATC TCTTTTTTTT CTAATAATTT CTTGAGCTAA G

OLIGO 9
TCGACAAACA TTCTACTGGT GGTGTTGGTG ATGTTACTTC TTTAATGTTA GGTCCAATGG TTGCTGCTTG TGG

OLIGO 10
TTGGTTACATT CCAATGATTT CTGGTAGAGG TTTAGGTCAT ACTGGTGGTA CTTTAGATAA ATTAGAATCT

OLIGO 11
ATTCCAGGTT TCGATATTTT CCCAGATGAT AACAGATTCA GAGAAATTAT TAAAGATGTT GGTGTTGCTA

OLIGO 12
TTATTGGTCA AACTTCTTCT TTAGCTCCAG CTGATAAAAG ATTCTACGAT ACTAGAGATA TTACTGCTAC

OLIGO 13
TGTTGATTCA ATTCCATTAA TTACTGCTTC TATTTTAGCT AAAAAAATAG CTGAAGGTTT AGATGCTTTA

OLIGO 14
GTTATGGATG TTAAAGTTGG TTCTGGTGCT TTCTGCCAA CTACGAATT ATCTGAAGCC TTGGCTGAAG CGAT

FIG_2

OLIGO 15
CGCTTCAGCC AAGGCTTCAG ATAATVGTA AGTTGGCATG AAAGCACCAG AACCAACTTT AA

OLIGO 16
CATCCATAAC TAAAGCATCT AAACCTTCAG CTAATTTTTT AGCTAAAATA GAAGCAGTAA TTAATGGAAT

OLIGO 17
AGAATCAACA GTAGCAGTAA TATCTCTAGT AGCGTAGAAT CTTTTATCAG CTGGAGCTAA AGAAGAAGTT

OLIGO 18
TGACCAATAA TAGCAACACC AACATCTTTA ATAATTTCTC TGAATCTGTT ATCATCTGGG AAAATATCGA

OLIGO 19
AACCTTGGAAT AGATTCTAAT TTATCTAAAG TACCACCAGT ATGACCTAAA CCTCTACCAG AAATCATTGG

OLIGO 20
AATGTAACCA CCACAAGCAG CAACCATTGG ACCTAACATT AAAGAAGTAA CATCACCAAC ACCACCAGTA GAATGTTTG

OLIGO 21
CGTTGGTGTT GCTAACGGTG CTGGTGTTAG AACTACTGCT TTATTAACTG ATATGAACCA AGTTTT

OLIGO 22
AGCTTCTTCT GCTGGTAACG CTGTTGAAGT TAGAGAAGCT GTTCAATTCT TAACTGGTGA ATACAGAAAC

OLIGO 23
CCAAGATTAT TCGATGTTAC TATGGCTTTA TGTGTTGAAA TGTTAATTTC TGGTAAATTA GCTAAAGATG

OLIGO 24
ATGCTGAAGC TAGAGCTAAA TTACAAGCTG TTTTAGATAA CGGTAAAGCT GCTGAAGTTT TCGGTAGAAT

OLIGO 25
GGTTGCTGCT CAAAAAGGTC CAACTGATTT CGTTGAAAAC TACGCTAAAT ACTTACCAAC TGCTATGTTA

OLIGO26
ACTAAAGCTG TTTACGCTGA TACTGAAGGT TTCGTTTCTG AAATGGATAC TAGAGCTTTA GGTATGGCTG

OLIGO 27
TTGTTGCTAT GGGTGGTGGT AGAAGACAAG CCTCTGATAC TATTGATTAC TCTGTTGGTT TCACTGATAT

OLIGO 28
GGCTAGATTA GGTGATCAAG TTGATGGTCA AGACCATTA GCTGTTATTC ATGCTAAAGA TGAAAAACAAC

FIG_2A

OLIGO 29
TGGCAAGAAG CTGCTAAAGC TGTTAAAGCT GCTATTAAAT TAGCTGATAA AGCTCCAGAA

OLIGO 30
TCTACTCCAA CTGTTTACAG AAGGATGTC

OLIGO 31
GATATCCTTC TGTAAACAGT TGGAGTAGAT TCTGGAGCTT

OLIGO 32
TATCAGCTAA TTTAATAGCA GCTTTAACAG CTTTAGCAGC TTCTTGCCAG TTGTTTTCAT

OLIGO 33
CTTTAGCATG AATAACAGCT AATGGTCTTT GACCATCAAC TTGATCACCT AATCTAGCCA TATCAGTGA

OLIGO 34
AACCAACAGA GTAATCAATA GTATCAGAGG CTTGTCTTCT ACCACCACCC ATAGCAACAA CAGCCATACC T

OLIGO 35
AAAGCTCTAG TATCCATTTC AGAAACGAAA CCTTCAGTAT CAGCGTAAAC AGCTTTAGTT AACATAGCAG

OLIGO 36
TTGGTAAGTA TTTAGCGTAG TTTTCAACGT AATCAGTTGG ACCTTTTGA GCAGCAACCA TCTACCGAA

OLIGO 37
AACTTCAGCA GCTTTACCGT TATCTAAAAC AGCTTGTAAT TTAGCTCTAG CTTCAGCATC ATCTTTAGCT

OLIGO 38
AATTTACCAG AAATTAACAT TTCAACACAT AAAGCCATAG TAACATCGAA TAATCTTGGG TTTCTGTAT

OLIGO 39
TCACCAGTTA AGAATTGAAC AGCTTCTCTA ACTTCAACAG CGTTACCAGC AGAAGAAGCT AAAACTTGGT T

OLIGO40
CATATCAGTT AATAAAGCAT TAGTTCTAAC ACCAGCACCG TTAGCAACAC CAACGAT

*FIG_2B*

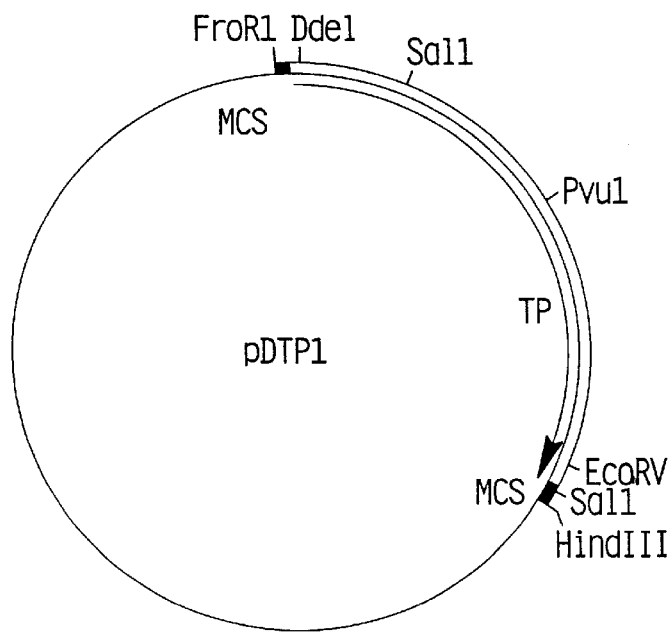
FIG_3
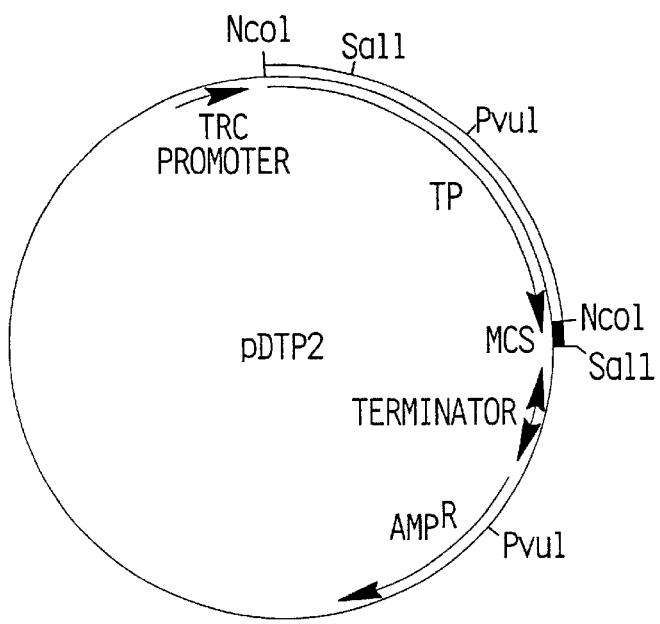
FIG_5

```
                    D
                    D
                    E
                    1                OLIGO 1
                    ┌──────────────────────────────────────────
                    CTTAGCTCAAGAAATTATTAGAAAAAAAAGAGATGGTCATGC
----,----+----,----+----,----+----,----+----,----+----,----+   50
                    GAATCGAGTTCTTTAATAATCTTTTTTTCTCTACCAGTACG
                    │LeuAlaGlnGluIleIleArgLysLysArgAspGlyHisAla
                    └──────────────────────────────────────────
                                  OLIGO 8
────────────────────────────────────────────────────────────
----,----+----,----+----,----+----,----+----,----+----,----+
                            │
TTTATCTGATGAAGAAATTAGATTCTTCATTAACGGTATTAGAGATAACA
----,----+----,----+----,----+----,----+----,----+----,----+  100
AAATAGACTACTTCTTTAATCTAAGAAGTAATTGCCATAATCTCTATTGT
 LeuSerAspGluGluIle│ArgPhePheIleAsnGlyIleArgAspAsnthr
────────────────────────────────────────────────────────────

----,----+----,----+----,----+----,----+----,----+----,----+
                     OLIGO 2
────────────────────────────────────────────────────────────┐
CTATTTCTGAAGGTCAAATTGCTGCTTTAGCTATGACTATTTTCTTCCAT
----,----+----,----+----,----+----,----+----,----+----,----+  150
GATAAAGACTTCCAGTTTAACGACGAAATCGATACTGATAAAAGAAGGTA
  IleSerGluGlyGlnIleAlaAlaLeuAlaMetThrI│lePhePheHis
                                       └────────────
                     OLIGO 7
----,----+----,----+----,----+----,----+----,----+----,----+
                     OLIGO 3
┌────────────────────────────────────────────────────────────
GATATGACTATGCCAGAAAGAGTTTCTTTAACTATGGCTATGAGAGATTC
----,----+----,----+----,----+----,----+----,----+----,----+  200
CTATACTGATACGGTCTTTCTCAAAGAAATTGATACCGATACTCTCTAAG
AspMetThrMetProGluArgValSerLeuThrMetAlaMetArgAspSer
────────────────────────────────────────────────────────────
                     OLIGO 6
----,----+----,----+----,----+----,----+----,----+----,----+
```

FIG_4

FIG. 4A

```
                                                        S
                                                        A
                                                        L
                              OLIGO 4                   1
        ────────────────────────────────────────────
        TGGTACTGTTTTAGATTGGAAATCTTTACATTTAAACGGTCCAATTGTCG
        ────,────+────,────+────,────+────,────+────,────+   250
        ACCATGACAAAATCTAACCTTTAGAAATGTAAATTTGCCAGGTTAACAGC
          GlyThrVa|LeuAspTrpLysSerLeuHisLeuAsnGlyProIleValAsp
                                      OLIGO 5
        ────,────+────,────+────,────+────,────+────,────+
                              OLIGO 9
        ─────────────────────────────────────────────
        ACAAACATTCTACTGGTGGTGTTGGTGATGTTACTTCTTTAATGTTAGGT
        ────,────+────,────+────,────+────,────+────,────+   300
        TGTTTGTAAGATGACCACCACAACCACTACAATGAAGAAATTACAATCCA
         |LysHisSerThrGlyGlyValGlyAspValThrSerLeuMetLeuGly
                              OLIGO 20
        ────,────+────,────+────,────+────,────+────,────+
        ─────────────────────────────────────────────
        CCAATGGTTGCTGCTTGTGGTGGTTACATTCCAATGATTTCTGGTAGAGG
        ────,────+────,────+────,────+────,────+────,────+   350
        GGTTACCAACGACGAACACCACCAATGTAAGGTTACTAAAGACCATCTCC
         ProMetValAlaAlaCysGlyGlyTyrIle|ProMetIleSerGlyArgGly

────,────+────,────+────,────+────,────+────,────+
                              OLIGO 10
        ─────────────────────────────────────────────
        TTTAGGTCATACTGGTGGTACTTTAGATAAATTAGAATCTATTCCAGGTT
        ────,────+────,────+────,────+────,────+────,────+   400
        AAATCCAGTATGACCACCATGAAATCTATTTAATCTTAGATAAGGTCCAA
          LeuGlyhisThrGlyGlyThrLeuAspLysLeuGluSerIleProGlyPhe
                              OLIGO 19
        ────,────+────,────+────,────+────,────+────,────+
                              OLIGO 11
        ─────────────────────────────────────────────
        TCGATATTTTCCCAGATGATAACAGATTCAGAGAAATTATTAAAGATGTT
        ────,────+────,────+────,────+────,────+────,────+   450
        AGCTATAAAAGGGTCTACTATTGTCTAAGTCTCTTTAATAATTTCTACAA
         |AspIlePheProAspAspAsnArgPheArgGluIleIleLysAspVal
                              OLIGO 18
        ────,────+────,────+────,────+────,────+────,────+
```

FIG. 4B

```
                                    OLIGO 12
         GGTGTTGCTATTATTGGTCAAACTTCTTCTTTAGCTCCAGCTGATAAAAG
         ----,----+----,----+----,----+----,----+----,----+   500
         CCACAACGATAATAACCAGTTTGAAGAAGAAATCGAGGTCGACTATTTTC
         GlyValAlaIleIleGlyGlnThrSerSerLeuAlaProAlaAspLysArg

----,----+----,----+----,----+----,----+----,----+

ATTCTACGCTACTAGAGATATTACTGCTACTGTTGATTCTATTCCATTAA
         ----,----+----,----+----,----+----,----+----,----+   550
         TAAGATGCGATGATCTCTATAATGACGATGACAACTAAGATAAGGTAATT
           PheTyrAlaThrArgAspIleThrAlaThrValAspSerIleProLeuIle
                   OLIGO 17
         ----,----+----,----+----,----+----,----+----,----+
                         OLIGO 13
         TTACTGCTTCTATTTTAGCTAAAAAATTAGCTGAAGGTTTAGATGCTTTA
         ----,----+----,----+----,----+----,----+----,----+   600
         AATGACGAAGATAAAATCGATTTTTTAATCGACTTCCAAATCTATGAAAT
           ThrAlaSerIleLeuAlaLysLysLeuAlaGluGlyLeuAspAlaLeu
                         OLIGO 16
         ----,----+----,----+----,----+----,----+----,----+
                         OLIGO 14
         GTTATGGATGTTAAAGTTGGTTCTGGTGCTTTCATGCCAACTTACGAATT
         ----,----+----,----+----,----+----,----+----,----+   650
         CAATACCTACAATTTCAACCAAGACCACGAAAGTACGGTTGAATGCTTAA
           ValMetAspValLysValGlySerGlyAlaPheMetProThrTyrGluLeu
                         OLIGO 15
         ----,----+----,----+----,----+----,----+----,----+

P
                         V
                         U
                         1         OLIGO 21
         ATCTGAAGCCTTGGCTGAAGCGATCGTTGGTGTTGCTAACGGTGCTGGTG
         ----,----+----,----+----,----+----,----+----,----+   700
         TAGACTTCGGAACCGACTTCGCTAGCAACCACAACGATTGCCACGACCAC
           SerGluAlaLeuAlaGluAlaIleValGlyValAlaAsnGlyAlaGlyVal
                                         OLIGO 40
         ----,----+----,----+----,----+----,----+----,----+
```

FIG. 4C

```
     TTAGAACTACTGCTTTATTAACTGATATGAACCAAGTTTTAGCTTCTTCT
     ----,----+----,----+----,----+----,----+----,----+   750
     AATCTTGATGACGAAATAATTGACTATACTTGGTTCAAAATCGAAGAAGA
      ArgThrThrAlaLeuLeuThrAspMet AsnGlnValLeuAlaSerSer

----,----+----,----+----,----+----,----+----,----+
                           OLIGO 22

GCTGGTAACGCTGTTGAAGTTAGAGAAGCTGTTCAATTCTTAACTGGTGA
     ----,----+----,----+----,----+----,----+----,----+   800
     CGACCATTGCGACAACTTCAATCTCTTCGACAAGTTAAGAATTGACCACT
      AlaGlyAsnAlaValGluValArgGluAlaValGlnPheLeuThrGlyGlu

OLIGO 39
     ----,----+----,----+----,----+----,----+----,----+
                           OLIGO 23

ATACAGAAACCCAAGATTATTCGATGTTACTATGGCTTTATGTGTTGAAA
     ----,----+----,----+----,----+----,----+----,----+   850
     TATGTCTTTGGGTTCTAATAAGCTACAATGATACCGAAATACACAACTTT
      TyrArgAsnProArgLeuPheAspValThrMetAlaLeuCysValGluMet

OLIGO 38
     ----,----+----,----+----,----+----,----+----,----+

TGTTAATTTCTGGTAAAATTAGCTAAAGATGATGCTGAAGCTAGAGCTAAA
     ----,----+----,----+----,----+----,----+----,----+   900
     ACAATTAAAGACCATTTAATCGATTTCTACTACGACTTCGATCTCGATTT
       LeuIleSerGlyLysLeuAlaLysAspAspAlaGluAlaArgAlaLys

----,----+----,----+----,----+----,----+----,----+
                           OLIGO 24

TTACAAGCTGTTTTAGATAACGGTAAAGCTGCTGAAGTTTTCGGTAGAAT
     ----,----+----,----+----,----+----,----+----,----+   950
     AATGTTCGACAAAATCTATTGCCATTTCGACGACTTCAAAAGCCATCTTA
      LeuGlnAlaValLeuAspAsnGlyLysAlaAlaGluVal PheGlyArgMet

OLIGO 37
     ----,----+----,----+----,----+----,----+----,----+
```

FIG_ 4D

```
          GGTTGCTGCTCAAAAAGGTCCAACTGATTTCGTTGAAAACTACGCTAAAT
          ----,----+----,----+----,----+----,----+----,----+    1000
          CCAACGACGAGTTTTTCCAGGTTGACTAAAGCAACTTTTGATGCGATTTA
          ValAlaAlaGlnLysGlyProThrAspPheValGluAsntyrAlaLysTyr
                          OLIGO 36
          ----,----+----,----+----,----+----,----+----,----+

ACTTACCAACTGCTATGTTAACTAAAGCTGTTTACGCTGATACTGAAGGT
          ----,----+----,----+----,----+----,----+----,----+    1050
          TGAATGGTTGACGATACAATTGATTTCGACAAATGCGACTATGACTTCCA
           LeuProThrAlaMetLeuThrLysAlaValTyrAlaAspThrGluGly
                          OLIGO 35
          ----,----+----,----+----,----+----,----+----,----+
                          OLIGO 26
          TTCGTTTCTGAAATGGATACTAGAGCTTTAGGTATGGCTGTTGTTGCTAT
          ----,----+----,----+----,----+----,----+----,----+    1100
          AAGCAAAGACTTTACCTATGATCTCGAAATCCATACCGACAACAACGATA
          PheValSerGluMetAspThrArgAlaLeuGlyMetAlaValValAlaMet

----,----+----,----+----,----+----,----+----,----+
                          OLIGO 27

GGGTGGTGGTAGAAGACAAGCCTCTGATACTATTGATTACTCTGTTGGTT
          ----,----+----,----+----,----+----,----+----,----+    1150
          CCCACCACCATCTTCTGTTCGGAGACTATGATAACTAATGAGACAACCAA
           GlyGlyGlyArgArgGlnAlaSerAspThrIleAspTyrSerValGlyPhe
                          OLIGO 34
          ----,----+----,----+----,----+----,----+----,----+
                          OLIGO 28
          TCACTGATATGGCTAGATTAGGTGATCAAGTTGATGGTCAAAGACCATTA
          ----,----+----,----+----,----+----,----+----,----+    1200
          AGTGACTATACCGATCTAATCCACTAGTTCAACTACCAGTTTCTGGTAAT
            ThrAspMetAlaArgLeuGlyAspGlnValAspGlyGlnArgProLeu
                          OLIGO 33
          ----,----+----,----+----,----+----,----+----,----+
```

FIG. 4E

```
GCTGTTATTCATGCTAAAGATGAAAACAACTGGCAAGAAGCTGCTAAAGC
----,----+----,----+----,----+----,----+----,----+   1250
CGACAATAAGTACGATTTCTACTTTTGTTGACCGTTCTTCGACGATTTCG

AlaValIleHisAlaLysAspGluAsnAsnTrpGlnGluAlaAlaLysAla

----,----+----,----+----,----+----,----+----,----+
               OLIGO 29

TCTTAAAGCTGCTATTAAATTAGCTGATAAAGCTCCAGAATCTACTCCAA
----,----+----,----+----,----+----,----+----,----+   1300
ACAATTTCGACGATAATTTAATCGACTATTTCGAGGTCTTAGATGAGGTT

ValLysAlaAlaIleLysLeuAlaAspLysAlaProGluSerThrProThr

OLIGO 32                          OLIGO 31
----,----+----,----+----,----+----,----+----,---+

E
              C
              R
   OLIGO 30   V
CTGTTTACAGAAGGATATC
----,----+----,----   1319
GACAAATGTCTTCCTATAG

ValTyrArgArgIle

----,----+----,----
```

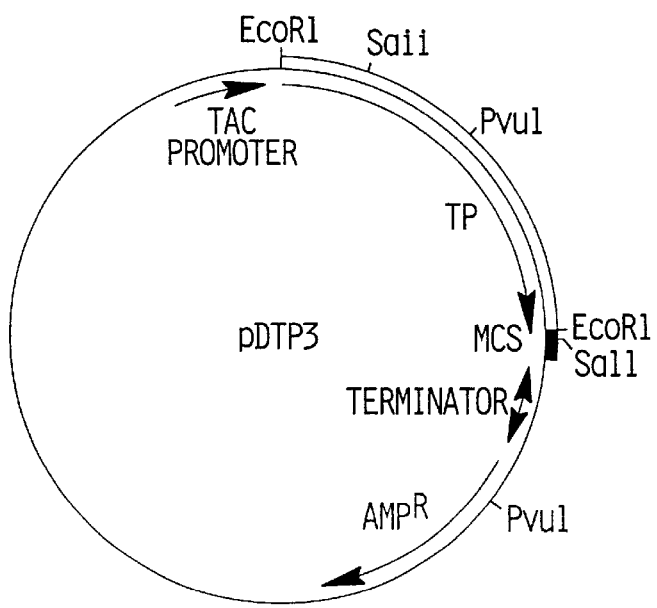
FIG_6
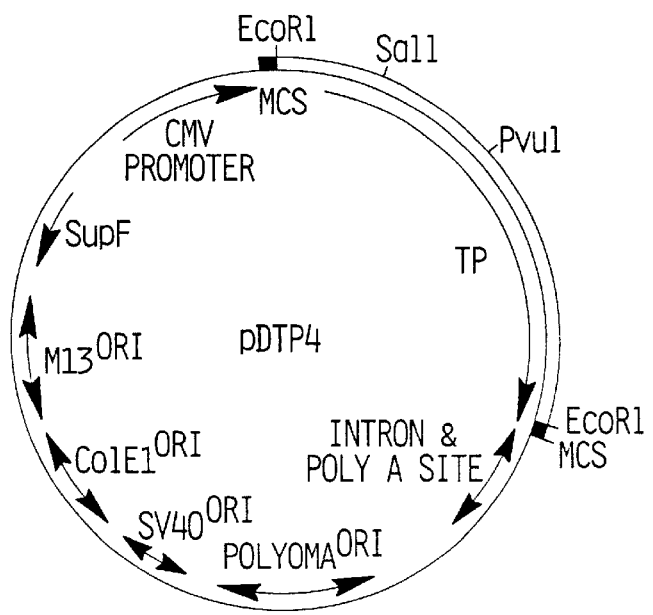
FIG_7

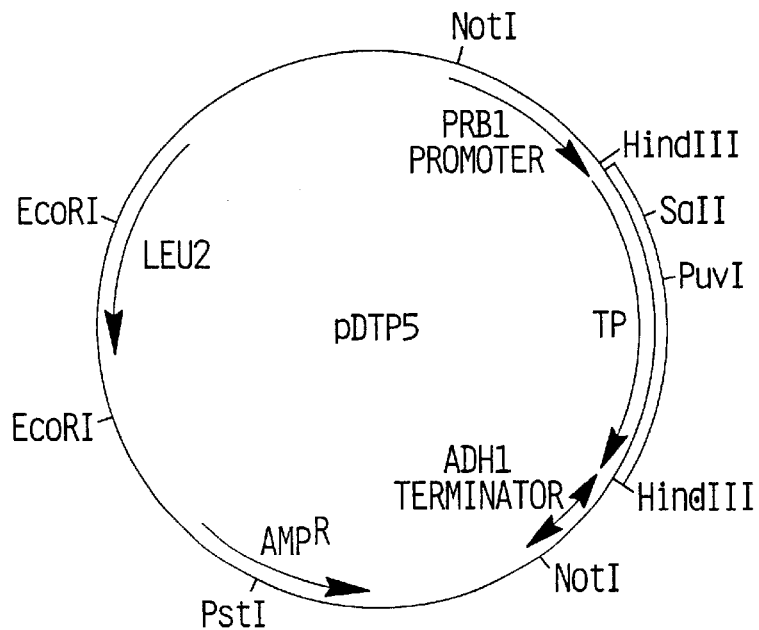
FIG_8
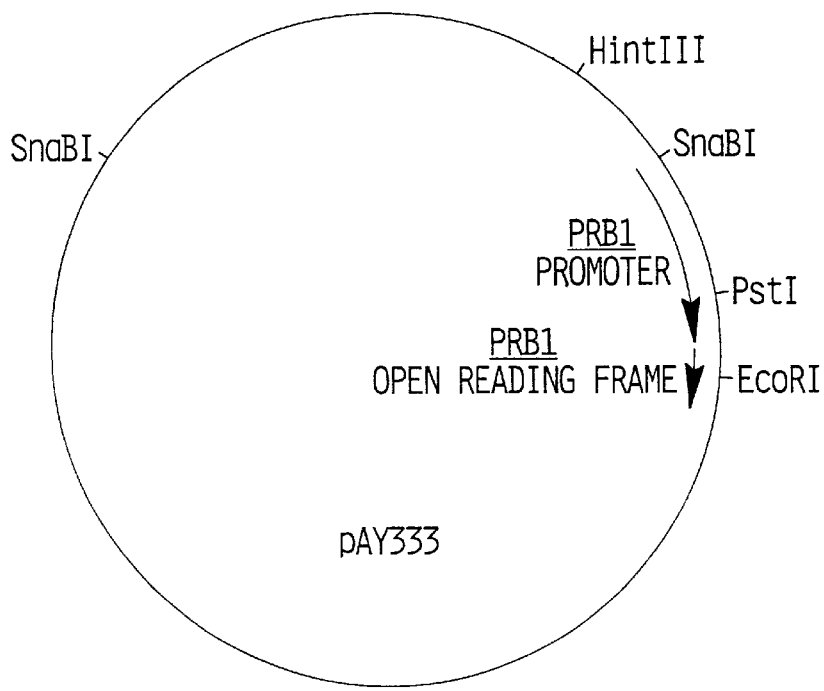
FIG_9

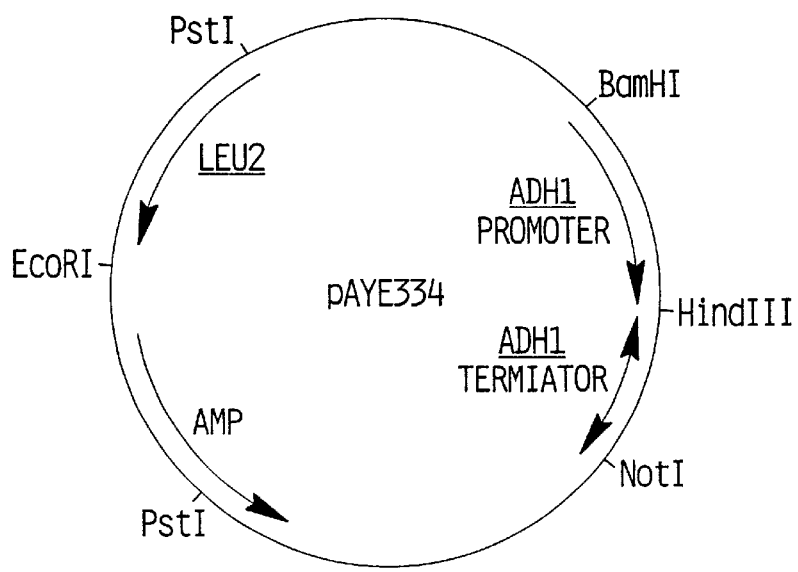
FIG_10
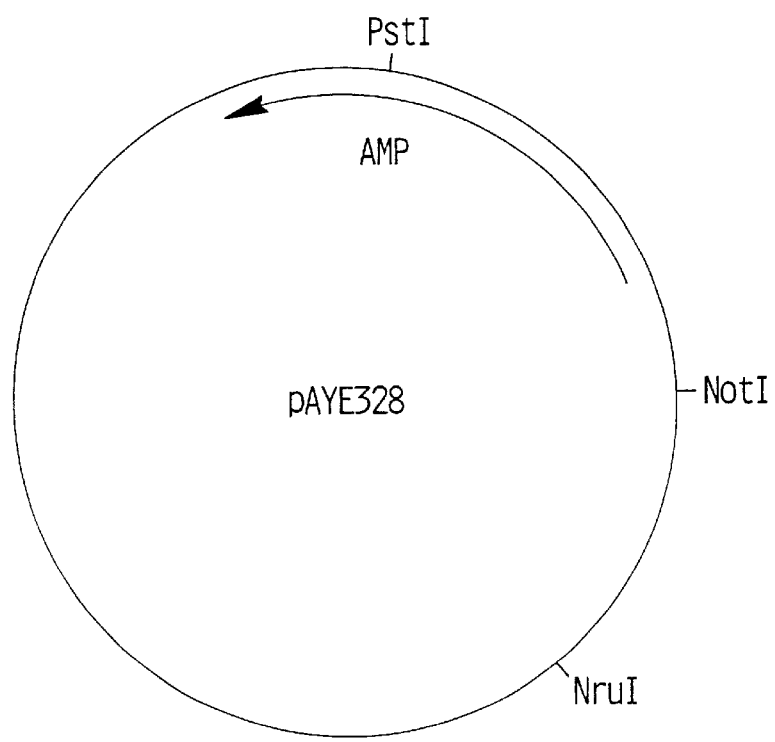
FIG_11

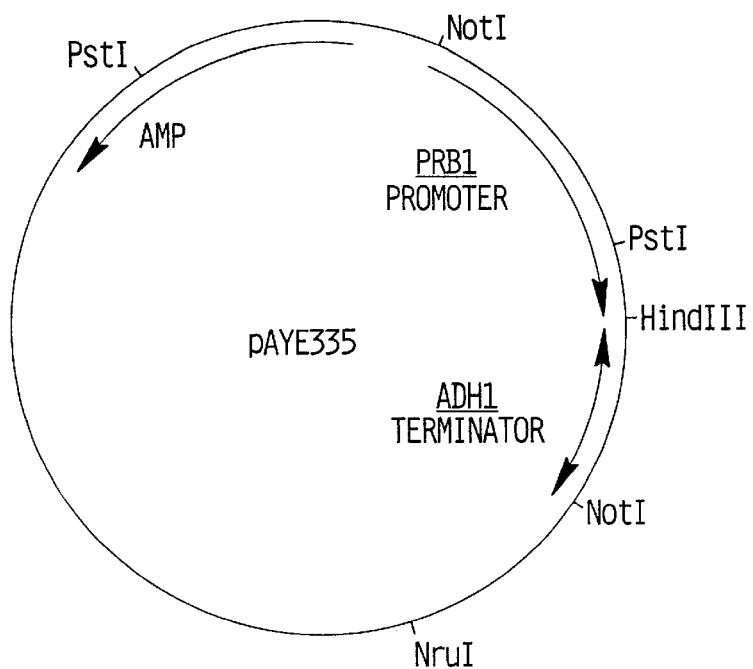
FIG_12
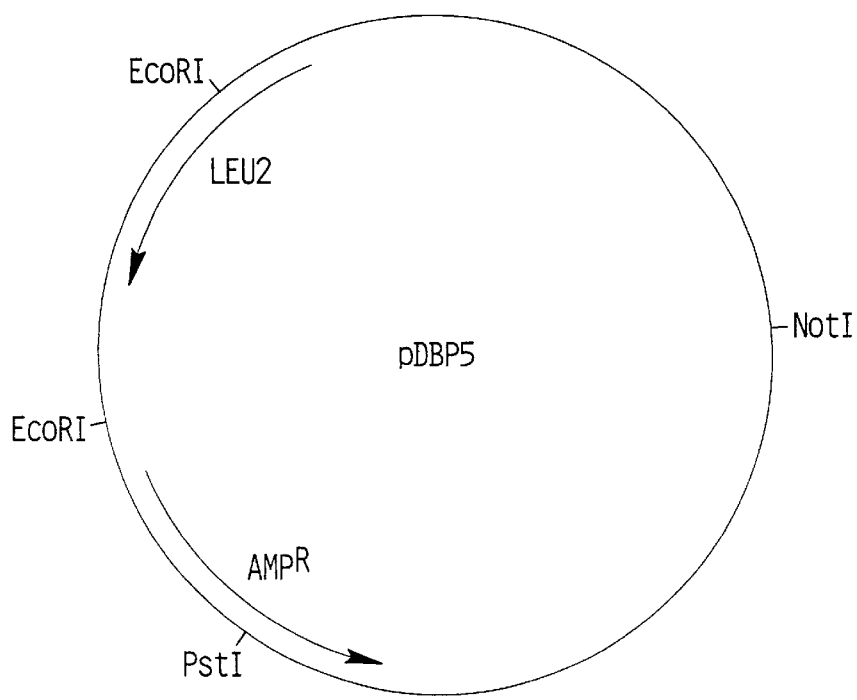
FIG_13

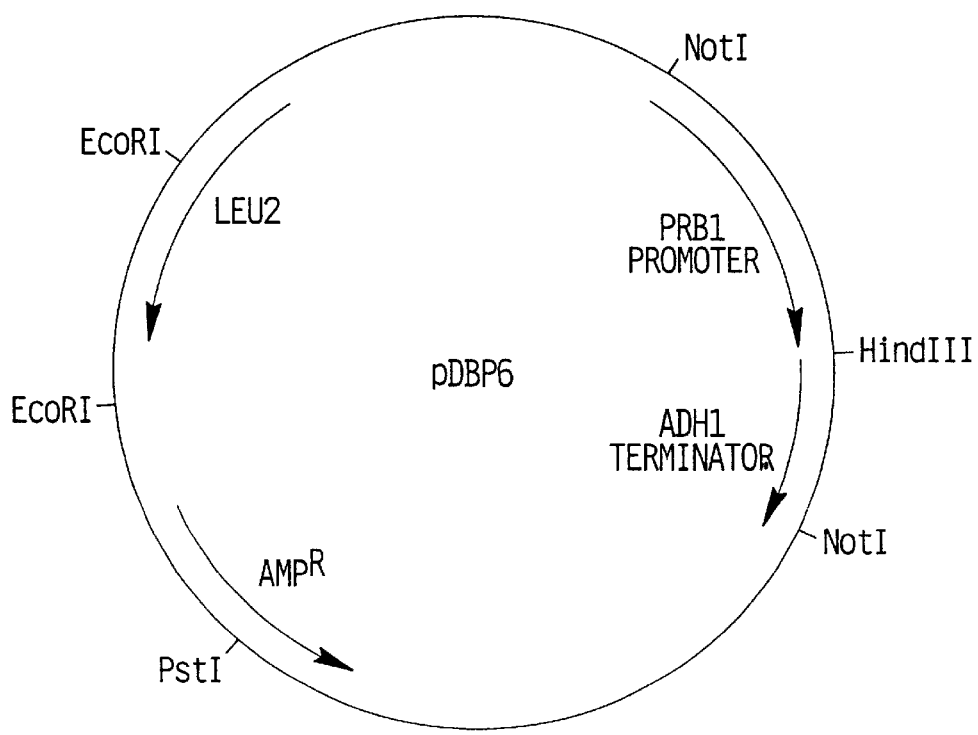
FIG_14
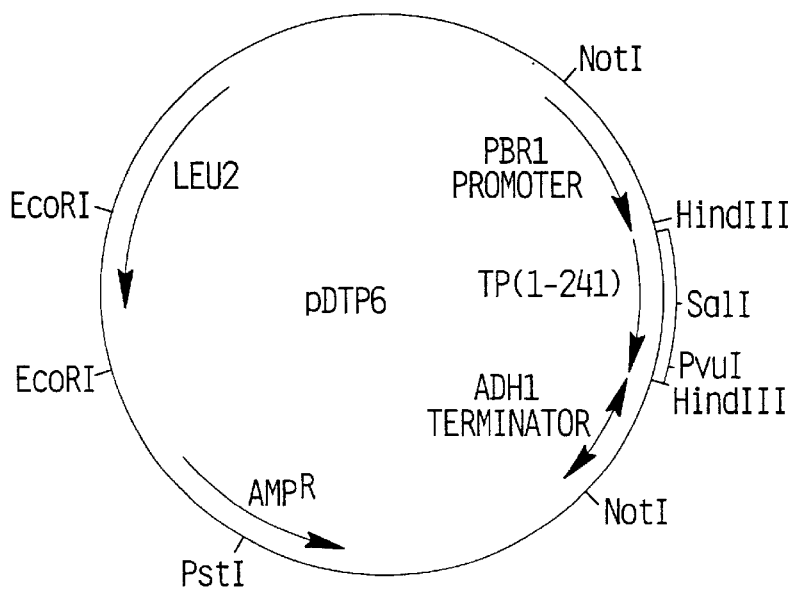
FIG_15

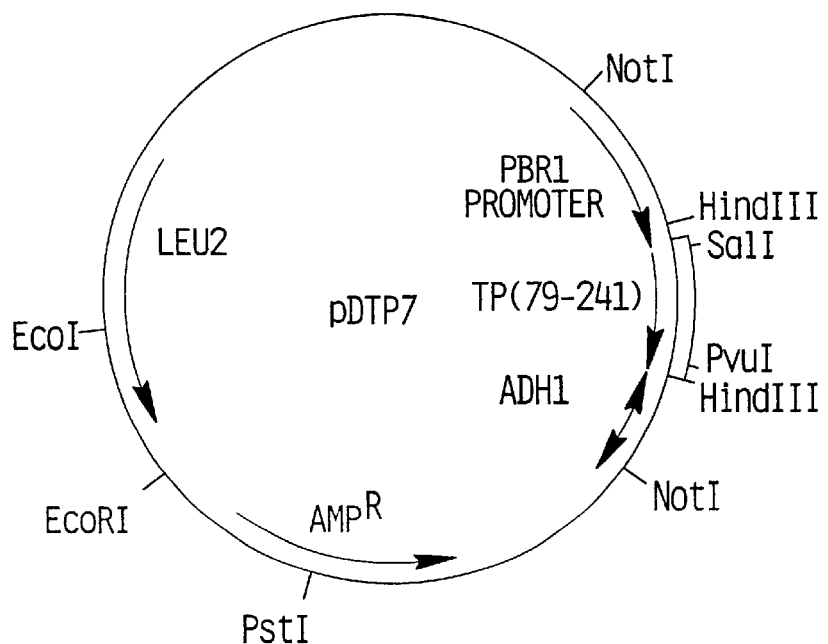
FIG_16
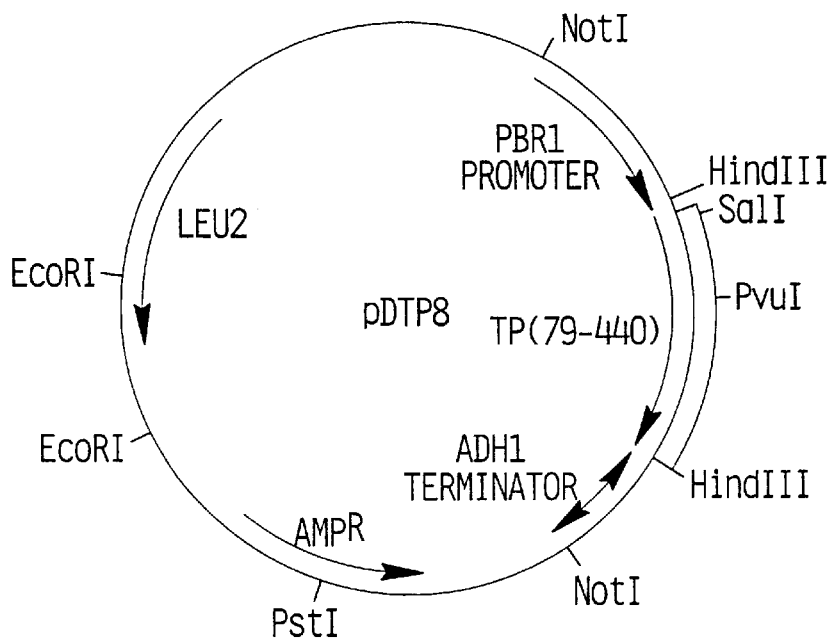
FIG_17

REGION 82-92

```
                                              CANCTRT
----,----+----,----+----,----+----,----+----,----+    250
                                              CANCTRT
                                              ←
                                              ValAspLys

----,----+----,----+----,----+----,----+----,----+

→
  ARCAYWSNACNGGNGGNGTNGGNGAY
  ----,----+----,----+----,- 276
  TYGTRWSNTGNCCNCCNCANCCNCTR
  HisSerThrGlyGlyValGlyAsp

----,----+----,----+----,-
```

*FIG_18A*

REGION 110-133

```
                                →
                       CCNATGATHWSNGGNMGNGGNYT
----,----+----,----+----,----+----,----+----+    350
                       GGNTACTADWSNCCNKCNCCNRA
                       ←
                       ProMetIleSerGlyArgGlyLeu

----,----+----,----+----,----+----,----+----+

NGGNCAYACNGGNGGNACNYTNGAYAARYTNGARWSNATHCCNGGNTTY
----,----+----,----+----,----+----,----+----,----    399
NCCNGTRTGNCCNCCNTGNRANCTRTTYRANCTYWSNTADGGNCCNAAR
GlyHisThrGlyGlyThrLeuAspLysLeuGluSerIleProGlyPhe

----,----+----,----+----,----+----,----+----,----+
```

*FIG_18B*

REGION 171-196

```
         →
     MGNGAYATHACNGCNACNGTNGAYWSNATHCCNYTNATHA
----,----+----,----+----,----+----,----+----,----+  550
     KCNCTRTADTGNCGNTGNCANCTRWSNTADGGNRANTADT
                                    ←
     ArgAspIleThrAlaThrValAspSerIleProLeuIleThr

----,----+----,----+----,----+----,----+----,----+

CNGCNWSNATHYTNGCNAARAARYTNGCNGARGGNYTN
----,----+----,----+----,----+----,----+---        588
GNCGNWSNTADRANCGNTTYTTYRANCGNCTYCCNRAN

AlaSerIleLeuAlaLysLysLeuAlaGluGlyLeu

----,----+----,----+----,----+----,---
```

```
Y = C OR T
R = A OR G
W = A OR T
S = C OR G
K = T OR G
M = C OR A
D = NOT C
V = NOT T
H = NOT G
B = NOT A
N = ANY BASE
```

FIG_18C

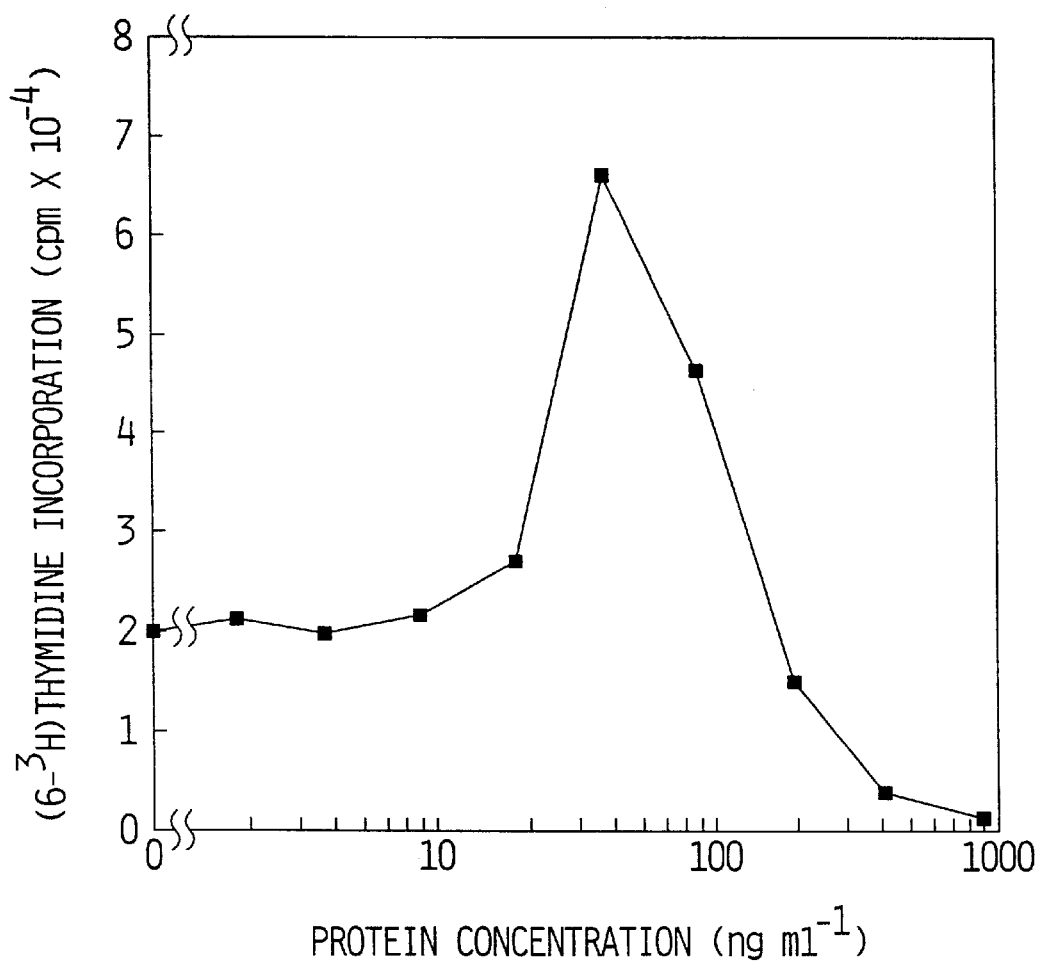
FIG_19

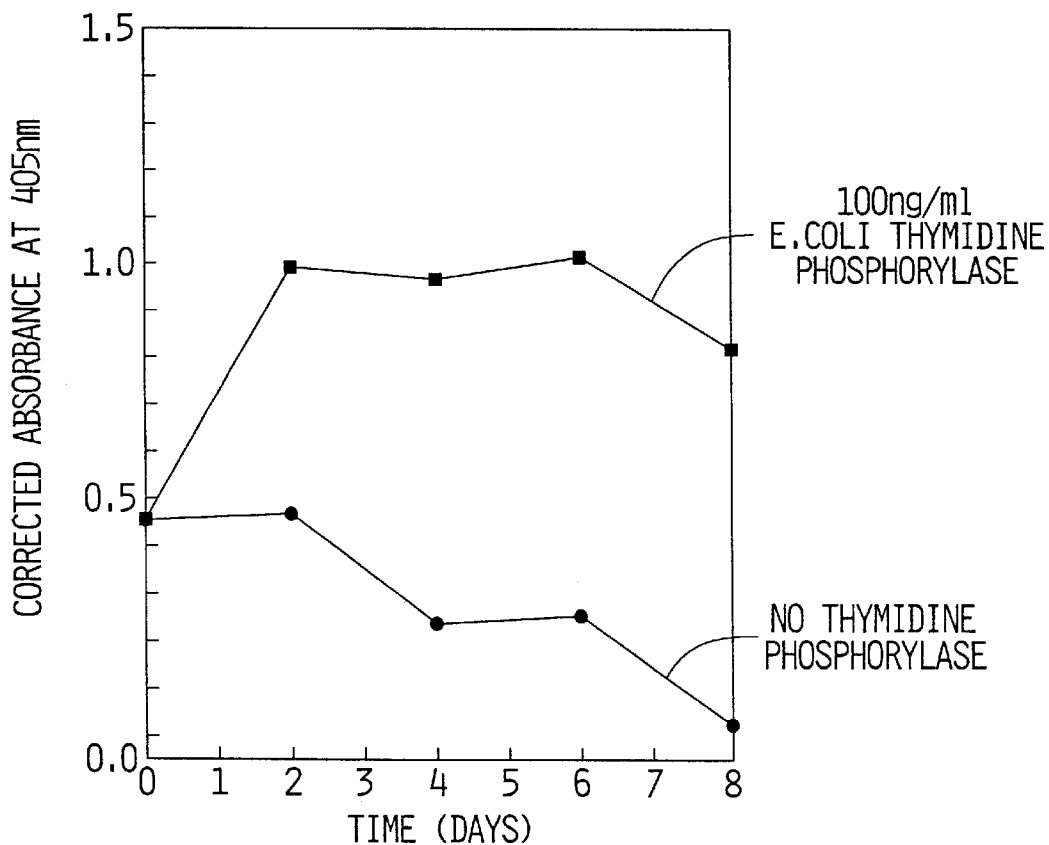
FIG_20

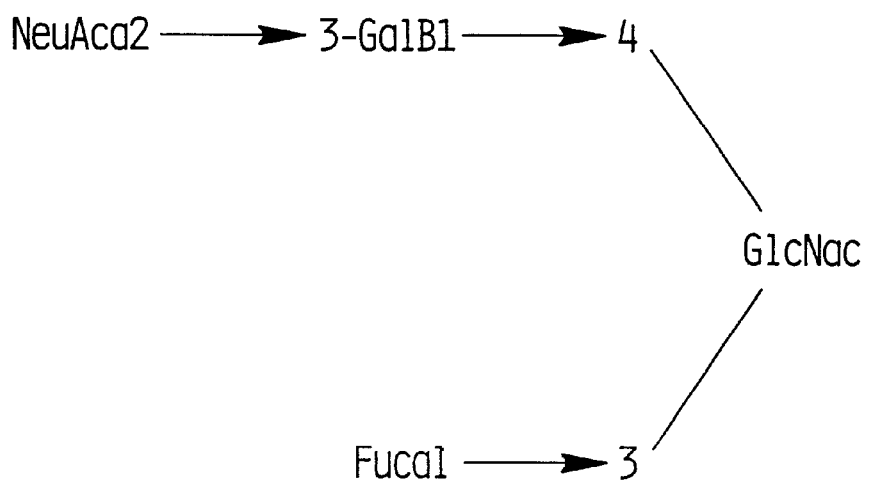
FIG_21A
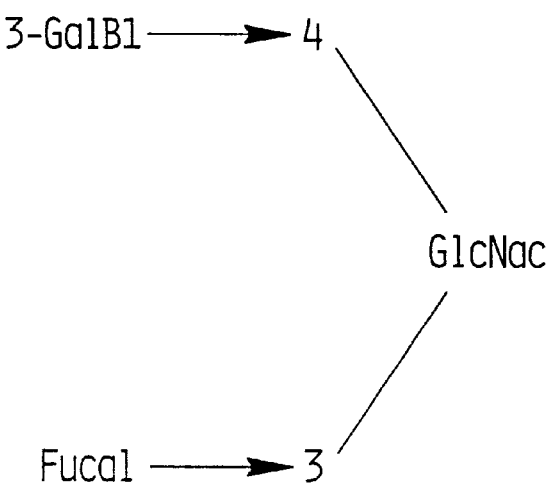
FIG_21B

MODULATION OF CELLULAR PROLIFERATION WITH THYMIDINE PHOSPHORYLASE

RELATED APPLICATIONS

This application is a continuation-in-part of U.S. patent application Ser. No. 08/211,860, filed Jun. 30, 1994 abandoned, which is a 371 of PCT/GB92/01887 filed Oct. 15, 1992, now abandoned.

The present invention relates to the medical use of thymidine phosphorylase in the modulation of cellular proliferation.

BACKGROUND OF THE INVENTION

Thymidine phosphorylase (thymine: orthophosphate deoxyribosyl transferase, EC 2.4.2.4) is a cytosolic enzyme which catalyses the reversible phosphorolysis of thymidine and other pyrimidine 2'-deoxyribosides, except for 4-amino substituted compounds such as 2'-deoxycytidine, as follows:

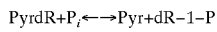

The phosphorolytic and synthetic reactions may also be used to transfer a deoxyribose moiety of one deoxynucleoside to form a second deoxynucleoside in a nucleoside deoxyribosyl transferase reaction (Schwartz, M. (1971) *Eur. J. Biochem.* 21, 191–198).

Thymidine phosphorylase has been purified and characterized from a number of micro-organisms (Schwartz, M. (1971) *Eur. J. Biochem.* 21, 191–198, Schwartz, M. (1978) *Methods Enzymol.* 51, 442–445; Avraham, Y. et al (1990) *Biochim. Biophys. Acta* 1040, 287–293; Hoffee, P. A. et al (1978) *Methods Enzymol.* 51, 437–442) and from human tissues (Desgranges, C. et al (1981) *Biochim. Biophys. Acta.* 654, 211–218; Kubilus, J. et al (1978) *Biochim. Biophys. Acta* 527, 221–228; Yoshimura et al (1990) *Biochim. Biophys. Acta* 1034, 107–113). *Escherichia coli* thymidine phosphorylase is a dimer of 90 kD composed of two identical subunits with a molecular weight of 45 kD (Schwartz, M. (1978) *Methods Enzymol.* 51, 442–445; Walter, M. et al (1990) *J. Biol. Chem.* 265, 14016–14022). The three-dimensional crystal structure of *Escherichia coli* has been determined to resolution of 2.8 Å (Walter, M. et al (1990) *J. Biol. Chem.* 265, 14016–14022). The monomer subunit consists of a small α-helical domain and a large α/β domain. The active site, which binds both thymidine and phosphate, has been located in a cleft between the two domains.

Human thymidine phosphorylase has been identified in many tissues including lymphocytes, heart, spleen, lung and placenta (Yoshimura, A. et al (1990) *Biochim. Biophys. Acta.* 1034, 107–113) and purified from both placenta (Yoshimura, A. et al (1990) *Biochim. Biophys. Acta.* 1034, 107–113; Kubilus, J. (1978) *Biochem. Biophys. Acta.* 527, 221–228) and platelets (Desgranges, C. (1981) *Biochim. Biophys. Acta* 654, 211–218). It has been suggested that thymidine phosphorylase plays an essential role in maintaining intracellular thymidine homeostasis (Shaw, T. et al (1988) *Mutant Res.* 200, 99–116). The thymidine salvage pathway requires the action of a permease to transport thymidine across the lipid bilayer. Intracellular thymidine is then phosphorylated by thymidine kinase, generating thymidine monophosphate (TMP) which is further phosphorylated to generate thymidine triphosphate.

Thymidine triphosphate not only regulates the thymidine salvage pathway by inhibition of thymidine kinase, but also inhibits the production of other deoxyribonucleotides by allosteric effects on ribonucleotide diphosphate reductase. The action of thymidine phosphorylase may therefore be to regulate the size of the intracellular thymidine nucleotide pool and hence the size of the other nucleotide pools via ribonucleotide diphosphate reductase as suggested by Shaw, T. et al, *Mutant Res.* 200, 99–116 (1988), and hence regulate DNA synthesis.

There has been no suggestion that thymidine phosphorylase could be used as an extracellular growth factor in medicine.

SUMMARY OF THE INVENTION

In accordance with the present invention, there is provided a method of modulating cellular proliferation by the application of a thymidine phosphorylase to an organism. In a further aspect of the subject method, the thymidine phosphorylase is a conjugate which includes a targeting portion adapted to target the conjugate to a specific cell type or anatomical location.

BRIEF DESCRIPTION OF THE DRAWINGS

FIG. 1 shows the amino acid sequence of *E. coli* thymidine phosphorylase;

FIGS. 2, 2A and 2B show the nucleotide sequences of Oligonucleotides 1 to 40;

FIG. 3 shows the construction of plasmid pDTP1;

FIGS. 4, 4A, 4B, 4C, 4D and 4E show the nucleotide sequence ligated into pUC19 to form pDTP1 (FIG. 3);

FIGS. 5 to 17 show the construction of plasmids pDTP2, pDTP3, pDTP4, pDTP5, pAYE333, pAYE334, pAYE328, pAYE335, pDBP5, pDBP6, pDTP6, pDTP7 and pDTP8, respectively;

FIGS. 18A, 18B and 18C show the amino acids in various regions of *E. coli* thymidine phosphorylase, together with corresponding PCR primers;

FIG. 19 shows the effect of thymidine phosphorylase on HUVE cell mitogenesis (□ represents CPAE cells grown in the absence of thymidine phosphorylase; ■ represents cells grown in presence of 100 ng/ml thymidine phosphorylase);

FIG. 20 shows the effect of thymidine phosphorylase on CPAE cell proliferation; and FIGS. 21A and 21B show the terminal structure of the LewisX and sialylated LewisX counter receptor.

DETAILED DESCRIPTION OF THE INVENTION

Cellular proliferation as utilized herein is defined as being any increase in cell number in the assay using CPAE cells described in Example 5.

The thymidine phosphorylase utilized in the method of the invention may be native thymidine phosphorylase from a prokaryotic or eukaryotic source, or a fragment of the native enzyme having thymidine phosphorylase enzymatic activity, or any other polypeptide having thymidine phosphorylase activity. Thymidine phosphorylase enzymatic activity is defined herein as phosphorolysis and/or nucleoside deoxyribosyl transferase activity. Whole thymidine phosphorylase compounds or fragments may be generated by proteolytic cleavage or by recombinant DNA techniques. The thymidine phosphorylase useful in the method of the invention has a thymidine phosphorylase activity of at least about 5%, preferably at least about 50%, most preferably at least about 90%, of the activity of the native *E. coli* enzyme.

Thymidine phosphorylase activity is determined spectrophotometrically, relying on the thousand-fold difference in the molar extinction co-efficients of thymidine and thymine. In carrying out the determination, saturating amounts of thymidine (1 mM) and $KH_2PO_4$ (0.2M), pH 7.4 are combined in a suitable 1 ml reaction tube with either 0.1–5 µg/ml *E. coli* thymidine phosphorylase or 1–50 µg/ml human thymidine phosphorylase, and the reaction at 25° C. is followed by monitoring the decrease in absorbance at 290 nm. A decrease in absorbance of 1 corresponds to the conversion of a 1 mM solution of thymidine to thymine, thus the decrease in absorbance can be used to calculate the $V_{max}$ of the enzyme (µmoles $min^{-1}mg^{-1}$). The thymidine phosphorylase utilized in the method of the invention does not include nature-identical human thymidine phosphorylase since it possesses, at best, only about 5% of the activity of the native *E. coli* enzyme.

Domains of thymidine phosphorylase can also be expressed. Preferred regions include amino acids 80–130, and analogues thereof (although such analogues preferably retain one or more of amino acids $Lys_{84}$, $His_{85}$, $Ser_{86}$, $Ser_{95}$, $Ser_{113}$ and $Thr_{123}$); a region including amino acids 165–220, or an analogue thereof (preferably retaining one or more of $Arg_{171}$, $Ser_{186}$, and $Lys_{190}$); or both regions 80–130 and 165–220, see FIG. 1. Other preferred regions include amino acids 1–241, 79–241 and 79–440. These regions can be expressed, as individual polypeptides or as parts of larger polypeptides, as recombinant proteins in any one of a number of host expression systems including mammalian cells, *Escherichia coli* and *Saccharomyces cerevisiae* when appropriately adapted by provision of translation/transcription initiation and termination sequences.

The techniques for preparing the polypeptides possessing thymidine phosphorylase activity described above are within the skill of the art. Preferred fragments are as discussed above. However, it is likewise within the skill of the art to determine whether a given fragment or analogue meets the criteria of the present invention since the identification and characterization of thymidine phosphorylase were known prior to the subject invention. Hence, it is within the skill of the art utilizing known techniques to determine whether a given fragment possesses at least 5% of the thymidine phosphorylase activity of the native *E. coli* enzyme.

The thymidine phosphorylase utilized in the subject invention may be produced by recombinant DNA techniques in heterologous hosts. Preferably, the host lacks an endogenous thymidine phosphorylase which will facilitate purification of the heterologous thymidine phosphorylase. *Saccharomyces cerevisiae* may lack an endogenous thymidine phosphorylase. Hosts possessing thymidine phosphorylase can have the endogenous thymidine phosphorylase gene deleted, for example, by site-directed mutagenesis.

Although rapid cellular proliferation is a hallmark of certain disease states it is also a prerequisite of many normal cellular processes, e.g. in response to tissue damage. Localized, rapid tissue growth and tissue remodelling are required in the wound healing process, where the growth of endothelial cells and the regeneration of a vascular network are necessary following surgical intervention, or for the treatment of burns and ulcers. Endothelial cell regeneration is also required following various surgical techniques where damage or injury results to the endothelial cell lining of the vascular network, for example balloon angioplasty or coronary by-pass surgery; or where an endothelial cell lining has to be generated de novo, for example, on synthetic vascular grafts or prostheses.

The activity of a growth- or proliferation-promoting agent may be enhanced by causing it to be accumulated at the site where such activity is required. Further, such targeting may enable the dosage of the agent required to be reduced since, by accumulating the agent at the required site, the efficacy of a given dosage may be significantly enhanced. Thymidine phosphorylase can be localized by conjugating it with a targeting agent by use of cross-linking agents as well as by recombinant DNA techniques whereby the thymidine phosphorylase DNA sequence, or a functional portion of it, is cloned adjacent to the DNA sequence of the agent when the agent is a protein, and the conjugate expressed as a fusion protein. The targeting agent can be any monoclonal antibody, or active portion thereof, eg Fab or $F(ab')_2$ fragment, a ligand (natural or synthetic) recognized by an endothelial cell surface receptor or a functional portion thereof, or any other agent which interacts with protein or structures of the endothelial cell.

Suitable active antibody portions, e.g. Fab or $F(ab')_2$ fragments of antibodies, will retain antigen/target binding but have low non-specific binding. Fab or $F(ab')_2$ fragments may be obtained by protease digestion, for example using immobilized Protein A and pepsin/papain digestion using ImmunoPure Fab and ImmunoPure $F(ab')_2$ preparation kits (Pierce). Other active portions of antibodies may be obtained by reduction of the antibodies or antibody fragments into separate heavy and light chains.

Molecules targeted by thymidine phosphorylase/antibody conjugates or gene fusions can be endothelial cell surface molecules, extracellular matrix components, for example collagen, fibronectin or laminin, or other blood vessel wall structures. Examples of monoclonal antibodies raised to endothelial surface antigens are Tük3 (Dako) and QBend10 (Serotec) which recognize CD34, a glycosylated endothelial cell surface transmembrane protein. Other monoclonal antibodies raised to endothelial cell surface antigens include 9G11, JC70, and By126 (British Bio-technology) raised to CD31 (also known as PECAM-1) and ESIVC7 raised to the CD36 antigen, which is the thrombospondin receptor (Kuzu et al (1992) *J. Clin. Pathol.*45, 143–148). QBend20, QBend30 and QBend40 (Serotec) are further examples of other monoclonal antibodies which recognize endothelial cell surface antigens.

The endothelial cell surface molecules to which the targeting antibodies are raised can be non-specific and recognize a number of different endothelial cell types from different tissues, or can be specific for certain endothelial cell types. Antibody A10-33/1 (Serotec) recognizes endothelial cells in metastatic melanomas, H4-7/33 (Serotec) recognizes endothelial cells from small capillaries and a wide range of tumor cells, HM15/3 (Serotec) recognizes sinusoidal endothelial cells, and 1F/10 (Serotec) binds to a 250 kD surface protein on continuous endothelium. Antibodies raised to antigens involved in haemostasis and inflammation can also be used. Antibody 4D10 (Serotec) and BB11 (Benjamin et al (1990) *Biochem. Biophys. Res. Commun.* 171, 348–353) recognizes ELAM-1 present on endothelial cells in acute inflamed tissues. Antibody 4B9 (Carlo, T. and Harlan, J. (1990) *Immunol. Rev.* 114, 1–24) recognizes the VCAM adhesion protein. Antibody 84H10 (Makgabo, M. et al (1988) *Nature* 331, 86–88) recognizes the ICAM1 adhesion protein. Antibody EN7/58 (Serotec) recognizes antigens present on inflamed endothelium and on cells adhering to the endothelial cells. Antibody KG7/30 recognizes a FVIII related protein on endothelial surfaces of inflamed tissues and tumors.

The cytokines IL-1 and TNF stimulate cultured endothelial cells to acquire adhesive properties for various peripheral blood leukocytes in vitro (Bevilaqua, M. et al (1985) *J.*

Clin. Invest. 76, 2003; Schleimer, R. et al (1986) J. Immunol. 136, 649; Lamas, A. et al (1988) J. Immunol. 140, 1500; Bochner, B. et al (1988) J. Clin. Invest. 81, 1355). This adhesiveness is associated with the induction on endothelial cells of a number of adhesive molecules, including ICAM-1, ELAM-1, GMP-140 (also known as PADGEM or CD62) and VCAM-1. These adhesive molecules recognize counter receptors on the surface of the target cell. VCAM-1 recognizes an antigen known as VLA-4, also known as CD49d/CD29 and member of the integrin family (Elices, M. et al (1990) Cell 60, 577; Schwartz, B. et al (1990) J. Clin. Invest. 85, 2019). ICAM-1 recognizes an antigen known as LFA-1, also known as CD11a/CD18, another member of the integrin family (Martin, S. et al (1987) Cell 51, 813–819 Fujita, H. et al (1991) Biochem. Biophys. Res. Comm. 177, 664–672). ELAM-1 and GMP-140 (GMP-140 is also known as CD62 or PADGEM), recognize an antigen known as LewisX, also known as CD15, or sialyl-LewisX (Larsen, E. et al (1990) Cell 63, 467–474; McEver, R. (1991) J. Cell. Biochem. 45, 156–161; Shimizu, Y. et al (1991) Nature 349, 799; Picker, L. et al (1991) Nature 349, 796–798; Polley, M. et al (1991) Proc. Natl. Acad. Sci. USA. 88, 6224–6228; Lowe, J. et al (1990) Cell 63, 475–484; Tiemeyer, M. et al (1991) Proc. Natl. Acad. Sci. USA. 88, 1138–1142).

Monoclonal antibodies to either the receptor expressed on the surface of the endothelial cell or counter receptor on the surface of the responding cell have been shown to block interaction of the components necessary for this cell-cell recognition and were instrumental in establishing the mode of recognition (for references see above).

A second aspect of this invention provides a conjugate of the thymidine phosphorylase as defined above and a moiety which specifically binds endothelial cells. Thymidine phosphorylase can be conjugated, by crosslinking or by recombinant DNA techniques, to natural or synthetic ligands which interact with receptors on the endothelial cell surface. Such ligands include growth factors, for example vascular permeability factor (Gitay-Goren, H. et al (1992) J. Biol. Chem. 267, 6093–6098; Bikfalin, A. et al (1991) J. Cell. Phys. 149, 50–59; Tischer, E. et al (1991) 266, 11947–11954; Conn, G. et al (1990) PNAS 87, 2628–2632; Keck, P. et al (1989) Science 246, 1309–1312; Leung, D. W. et al (1989) Science 246, 1306–1309); platelet-derived growth factor (Beitz, J. et al (1991) PNAS 88, 2021–2025); and well as other biomolecules such as transferrin and urokinase (Haddock, R. et al (1991) J. Biol. Chem. 266, 21466–21473). The ligand domain of the conjugates will be recognized by the endothelial cell surface receptor for that ligand and will target the thymidine phosphorylase to the endothelium.

An agent with thymidine phosphorylase activity, for example thymidine phosphorylase or a fragment of thymidine phosphorylase with thymidine phosphorylase activity as defined above, can also be directed toward a specific adhesion molecule by cross-linking the agent to the counter receptor for that adhesion molecule. In the example of ELAM-1 mediated adhesion, the counter receptor is a carbohydrate determinant known as Lewis-X or sialylated Lewis-X, the terminal structure of which is given in FIGS. 21A and 21B. Synthetic carbohydrates with this terminal structure (Kameyama, A. et al (1991) Carbohydrate. Res. 209, C1–C4) or purified from natural sources, for example LNFIII (Calbiochem), are available. The terminal Lewis-X or sialyl Lewis-X determinant can be cross-linked to free sulfydryl groups within the thymidine phosphorylase agent as described in Example 1. This allows specific targeting of the agent to endothelial cells presenting the ELAM-1 adhesion molecule.

This moiety may be a monoclonal antibody to endothelial cell surface receptors such as ICAM-1, ELAM-1, GMP-140 or VCAM-1. Alternatively, this moiety may be the counter receptor itself, or a functional portion thereof. Fusion may be achieved by i) chemical cross linking of the moiety, be it a monoclonal antibody or the counter receptor, by techniques known in the art, or ii) by recombinant DNA technology whereby the moiety, when it is a single polypeptide chain, is expressed as a gene fusion with the agent in a suitable host.

A number of cell- or stage-specific antibodies have been described. These include, for example antibodies to endothelial cell adhesion molecules, including antibody BB11 (anti-ELAM, Benjamin, C. et al (1990), Biochem. Biophys. Res. Commun. 171, 348–353), antibody 4B9 (anti-VCAM, Carlo, T. and Harlan, J. (1990) Immunol. Rev. 114, 1–24) and antibody 84H10 (anti-ICAM1, Makgobo, M. et al (1988) Nature 331, 86–88). These antibodies, or antibodies like them, can be covalently joined to an agent with structural homology to thymidine phosphorylase, be it full length thymidine phosphorylase or a fragment of it with enzyme activity. This can be achieved by gene fusion whereby the DNA sequence encoding the agent with thymidine phosphorylase activity is spliced into the genes encoding either the heavy or light chain of the antibody. Alternatively, the agent can be covalently cross-linked to the antibody via one of a number of bi-functional cross-linking reagents such as, for example, disuccinimidyl suberate (DSS); bis (sulfosuccinimidyl) suberate ($BS^3$); dimethyl adipimidate-2 HCl (DMA); dimethyl pimelimidate-2 HCl (DMP); dimethyl suberimidate-2 HCl (DMS); bismaleimidohexane (BMH); m-maleimidobenzoyl-N-hydroxysuccinimide ester (MBS); m-maleimido-benzoyl-N-hydroxysulfosuccinimide ester (sulfo-MBS); succinimidyl 4-(p-maleimidophenyl) butyrate (SMPB); sulfosuccinimidyl 4-(p-maleimidophenyl) butyrate (sulfo-SMPB); N-succinimidyl (4-iodoacetyl) aminobenzoate (SIAB); sulfosuccinimidyl (4-iodoacetyl) aminobenzoate (sulfo-SIAB); succinimidyl 4-(N-maleimidomethyl)cyclohexane-1-carboxylate (SMCC); sulfosuccinimidyl 4-(N-maleimidomethyl) cyclohexane-1-carboxylate (Sulfo-SMCC) or 1,5-difluoro-2,4-dinitrobenzene (DFDNB), (Pierce).

While appropriate concentrations of thymidine phosphorylase can be demonstrated to stimulate mammalian cell growth, at superoptimal concentrations mitogenesis can be reduced or inhibited (FIG. 19). Therefore, by targeting thymidine phosphorylase to certain cell types where rapid or uncontrolled cellular proliferation is associated with certain disease states, proliferation of these cell types can be reduced.

Antibodies recognizing antigens related to malignant transformation and angiogenesis can also be used: for example EN2/3 (Serotec) recognizes an antigen characteristic of malignant transformed endothelial cells; EN7/44 (Serotec) recognizes an angiogenesis related antigen present on proliferating, migrating and budding endothelial cells; and H3-5/47 recognizes endothelial cells in angioblasts, angiomas, angiosarcomas and perivascular cells in psoriasis and arthritic tissues.

Alternatively, the entity which is recognized by the targeting portion may be a suitable entity which is specifically expressed by tumor cells, which entity is not expressed, or at least not with such frequency, in cells into which one does not wish to introduce the thymidine phosphorylase. The entity which is recognized will often be an antigen. Examples of antigens include those listed in Table 1 below. Monoclonal antibodies which will bind specifically to many of these antigens are already known (for example those given in the Table) but in any case, with today's techniques in relation to monoclonal antibody technology, antibodies can be prepared to most antigens. The antigen-specific portion may be an entire antibody (usually, for convenience and specificity, a monoclonal antibody), a part or parts thereof (for example an $F_{ab}$ fragment, $F(ab')_2$, dab or "minimum recognition unit") or a synthetic antibody or part thereof. A compound comprising only part of an antibody may be advantageous by virtue of being less likely to undergo non-specific binding due to the $F_c$ part.

Suitable monoclonal antibodies to selected antigens may be prepared by known techniques, for example those disclosed in "Monoclonal Antibodies: A manual of techniques", H. Zola (CRC Press, 1988) and in "Monoclonal Hybridoma Antibodies: Techniques and Applications", J. G. R. Hurrell (CRC Press, 1982). All references mentioned in this specification are incorporated herein by reference. Bispecific antibodies may be prepared by cell fusion, by reassociation of monovalent fragments or by chemical cross-linking of whole antibodies, with one part of the resulting bispecific antibody being directed to the cell-specific antigen and the other to the thymidine phosphorylase. The bispecific antibody can be administered bound to the thymidine phosphorylase or it can be administered first, followed by the thymidine phosphorylase. The former is preferred. Methods for preparing bispecific antibodies are disclosed in Corvalan et al (1987) *Cancer Immunol. Immunother.* 24, 127–132 and 133–137 and 138–143. Bispecific antibodies, chimaeric antibodies and single chain antibodies are discussed generally by Williams in *Tibtech*, February 1988, Vol. 6, 36–42, Neuberger et al (*8th International Biotechnology Symposium*, 1988, Part 2, 792–799) and Tan and Morrison (*Adv. Drug Delivery Reviews* 2, (1988), 129–142). Suitably prepared non-human antibodies can be "humanized" in known ways, for example by inserting the CDR regions of mouse antibodies into the framework of human antibodies. IgG class antibodies are preferred.

TABLE 1

| Antigen | Antibody | Existing Uses |
|---|---|---|
| 1. Tumor Associated Antigens | | |
| Carcino-embryonic Antigen | {C46 (Amersham) {85A12 (Unipath) | Imaging & Therapy of colon/rectum tumors. |
| Placental Alkaline Phosphatase | H17E2 (ICRF, Travers & Bodmer | Imaging & Therapy of testicular and ovarian cancers. |
| Pan carcinoma | NR-LU-10 (NeoRx Corporation) | Imaging & Therapy of various carcinomas incl. small cell lung cancer. |
| Polymorphic Epithelial Mucin (Human milk fat globule) | HMFG1 (Taylor-Papadimitriou, ICRF) | Imaging & Therapy of ovarian cancer, pleural effusions. |
| β-human Chorionic Gonadotropin | W14 | Targeting of enzyme (CPG2) to human xenograft choriocarcinoma in nude mice. (Searle et al (1981) Br. J. Cancer 44, 137–144). |
| a Carbohydrate on Human Carcinomas | L6 (IgG2a)[1] | Targeting of alkaline phosphatase. (Senter et al (1988) P.N.A.S. 85, 4842–4846. |
| CD20 Antigen on B Lymphoma (normal | 1F5 (IgG2a)[2] | Targeting of alkaline phosphatase. (Senter et al |

TABLE 1-continued

| Antigen | Antibody | Existing Uses |
|---|---|---|
| and neoplastic) | | (1988) P.N.A.S. 85, 4842–4846. |
| 2. Immune Cell Antigens | | |
| Pan T Lymphocyte Surface Antigen (CD3) | OKT-3 (Ortho) | As anti-rejection therapy for kidney transplants. |
| B-lymphocyte Surface Antigen (CD22) | RFB4 (Janossy, Royal Free Hospital) | Immunotoxin therapy of B cell lymphoma. |
| Pan T lymphocyte Surface Antigen (CD5) | H65 (Bodmer, Knowles ICRF, Licensed to Xoma Corp., USA) | Immunotoxin treatment of Acute Graft versus Host disease, Rheumatoid Arthritis. |

[1]Hellström et al (1986) Cancer Res. 46, 3917–3923
[2]Clarke et al (1985) P.N.A.S. 82, 1766–1770
Other antigens include alphafoetoprotein, Ca-125 and prostate specific antigen.

If applied to the treatment of CML or ALL, the ligand binding molecules can be monoclonal antibodies against leukaemia-associated antigens. Examples of these are: anti-CALLA (common acute lymphoblastic leukaemia-associated antigen), J5, BA-3, RFB-1, BA-2, SJ-9A4 Du-ALL-1, anti-3-3, anti-3-40, SN1 and CALL2, described in Foon, K. A. et al 1986 *Blood* 68(1), 1–31, "Review: Immunologic Classification of Leukemia and Lymphoma". The ligand binding molecules can also be antibodies that identify myeloid cell surface antigens, or antibodies that are reactive with B or T lymphocytes, respectively. Examples of such antibodies are those which identify human myeloid cell surface antigens or those which are reactive with human B or T lymphocytes as described in Foon, K. A. Id. Additional examples are antibodies B43, CD22 and CD19 which are reactive with B lymphocytes can also be used.

Alternatively, the entity which is recognized may or may not be antigenic but can be recognized and selectively bound to in some other way. For example, it may be a characteristic cell surface receptor such as the receptor for melanocyte-stimulating hormone (MSH) which is expressed in high numbers in melanoma cells. The targeting portion may then be a compound or part thereof which specifically binds to the entity in a non-immune sense, for example as a substrate or analogue thereof for a cell-surface enzyme or as a messenger. In the case of melanoma cells, the targeting portion may be MSH itself or a part thereof which binds to the MSH receptor. Such MSH peptides are disclosed in, for example, Al-Obeidi et al (1980) *J. Med. Chem.* 32, 174. The specificity may be indirect: a first cell-specific antibody may be administered, followed by a conjugate of the invention directed against the first antibody. Preferably, the entity which is recognized is not secreted to any relevant extent into body fluids, since otherwise the requisite specificity may not be achieved.

The targeting portion of the conjugate of this embodiment of the invention may be linked to the thymidine phosphorylase by any of the conventional ways of linking compounds, for example by disulfide, amide or thioether bonds, such as those generally described in Goodchild, supra or in Connolly (1985) *Nucl. Acids Res.* 13(12), 4485–4502 or in PCT/US85/03312.

When applied topically in accordance with the present invention, the thymidine phosphorylase can be incorporated into an inert cream or base so that it is stabilized. Such a vehicle facilitates even application of the thymidine phosphorylase and maintains the agent at the site of application. This can also be achieved by incorporation of the thymidine phosphorylase, optionally as a component of an inert cream or base, into a bandage or dressing. Alternatively, the thymidine phosphorylase can be applied topically in the form of an aerosol where the thymidine phosphorylase has been previously dissolved or resuspended in, for example, a saline solution. Such formulations can be used either to promote wound healing or to combat tumors. The pharmaceutical carrier may also take the form of a graft, to which the thymidine phosphorylase is cross-linked. More specifically in the case of combatting tumors, injectable formulations of the thymidine phosphorylase can be prepared.

The anti-tumor conjugates of the invention may be administered in any suitable way, usually parenterally, for example intravenously, intraperitoneally or, preferably (for bladder cancers), intra-vesically (ie into the bladder), or directly into the tumor, in standard sterile, non-pyrogenic formulations of diluents and carriers, for example isotonic saline (when administered intravenously). If needed, because the compound of the invention may be immunogenic, cyclosporin or some other immunosuppressant can be administered to provide a longer period for treatment but usually this will not be necessary.

Particular tumors suitable for treatment in accordance with the invention include cancers of the uterine cervix, head, neck, brain gliomas, breast, colon, oesophagus, stomach, liver, pancreas and metastatic forms of any of these.

The invention is further illustrated by the following examples, it being understood that the details given therein are not intended to limit the invention in any manner.

EXAMPLE 1

Expression of an Agent with Thymidine Phosphorylase Activity

Unless otherwise stated, all procedures were carried out as described by Maniatis, Fritsch and Sambrook, "Molecular Cloning: A Laboratory Handbook", Cold Spring Harbor Laboratory (1982).

The primary amino acid sequence of *Escherichia coli* thymidine phosphorylase, FIG. 1, has been described (Walter, M. et al (1990) *J. Biol. Chem.* 265, 14016–14022). A double stranded cDNA was prepared by annealing 40 overlapping single-stranded oligonucleotides. These were designed to encode the amino acid sequence of thymidine phosphorylase, as described by Walter, M. et al (1990), see above. The DNA sequence (5'→3') of oligonucleotides 1 to 40 is given in FIGS. 2 to 2B. Oligonucleotides 1 to 8 were prepared on an Applied Biosystems 380B DNA synthesiser. The oligonucleotides were phosphorylated by T4 polynucleotide kinase. Phosphorylated oligonucleotides 1 to 8 (25 pmol each) were annealed in water for 5 min at 60° C., following which the solution was allowed to cool to 15° C. over the next 60 min. The mixture was made up to 50 mM Tris/HCl pH7.5, 10 mM MgCl$_2$, 10 mM dithiothreitol, 1 mM ATP (DNA ligase buffer) and T4 DNA ligase added. The ligation was incubated at 15° C. for 18 hours. The ligated product (oligonucleotide duplex I) was purified from a 10% polyacrylamide gel, electrophoresed under nondenaturing conditions. Oligonucleotides 9 to 20 were phosphorylated and ligated in a similar way to generate oligonucleotide duplex II, while oligonucleotides 21 to 40, when phosphorylated and ligated, generated oligonucleotide duplex III. Oligonucleotide duplexes I, II and III were ligated into the SmaI site of pUC19, generating plasmid pDTP1 (FIG. 3). The sequence of the DNA insert is shown in FIGS. 4 to 4E. Two double-stranded oligonucleotide adapters, oligonucleotide duplexes IV and V, were prepared by annealing oligonucleotides 41 and 42, and oligonucleotides 43 and 44 respectively.

Oligonucleotide Duplex IV

```
5'-CATGTTATTC -3'  (oligo 41, SEQ42)

3'-   AATAAGAAT-5' oligonucleotide 42
```

Oligonucleotide Duplex V

```
5'-ATCTGAATAAC     -3' (oligo 43, SEQ43)

3'-TAGACTTATTGGTAC-5' (oligo 44, SEQ44)
```

These two adaptors, along with the 1.35 kbp DdeI-EcoRV thymidine phosphorylase DNA sequence from plasmid pDTP1, were ligated into the *Escherichia coli* expression vector pTrc99A (Pharmacia), digested with NcoI to generate plasmid pDTP2 (FIG. 5). The 1.34 kbp NcoI DNA insert encodes *Escherichia coil* thymidine phosphorylase with a translation initiation codon, 5'-ATG-3', inserted 5' to the leucine codon at amino acid position 1 (see FIG. 1) and a translation termination codon, 5'-TAA-3', inserted 3' to the glutamic acid codon at amino acid position 440 (see FIG. 1). Following the introduction of plasmid pDTP2 into *Escherichia coli* and selection for ampicillin-resistant transformants, thymidine phosphorylase can be expressed from the strong trc promoter.

By introducing EcoRI restriction recognition sites at each end of the synthetic thymidine phosphorylase DNA sequence, thymidine phosphorylase can be expressed from the IPTG inducible tac promoter system present in plasmid pKK223-3 (Pharmacia). This was achieved by the same methodology as described above for the trc promoter system. Two double-stranded oligonucleotide adaptors, oligonucleotide duplex VI and VII, were prepared by annealing oligonucleotides 45 and 46 and oligonucleotides 47 and 48, respectively.

Oligonucleotide Duplex VI

```
5'-AATTCATGTTATTC    -3'    (oligo 46, SEQ46)

3'-    GTACAATAAGAAT-5' (oligo 46, SEQ46)
```

Oligonucleotide Duplex VII

```
5'-ATCTGAATAAG    -3' (oligo 47, SEQ47)

3'-TAGACTTATTCTTAA-5' (oligo 48, SEQ48)
```

The two adaptors, along with the 1.315 kbp DdeI-EcoRV thymidine phosphorylase DNA sequence from plasmid pDTP1, were ligated into the *Escherichia coli* expression vector pKK223-3 (Pharmacia) digested with EcoRI, to generate plasmid pDTP3 (FIG. 6).

To facilitate expression of recombinant thymidine phosphorylase in mammalian cells, the 1.34 kbp EcoRI synthetic thymidine phosphorylase DNA sequence from plasmid pDTP3 was purified and ligated into the EcoRI site of the mammalian expression vector pcDNAI (Invitrogen Corporation), linearised with EcoRI. The resultant plasmid, pDTP4 (FIG. 7), once transfected into mammalian cells, for example CHO or COS-7, directs the expression of recombinant thymidine phosphorylase from the CMV promoter.

EXAMPLE 2

Expression in Yeast

*Saccharomyces cerevisiae* can be used as an alternative expression host. This host may offer distinct advantages over mammalian- or *Escherichia coli*-based heterologous expression systems in that *Saccharomyces cerevisiae* lacks any thymidine kinase activity (Grivell, A. R. and Jackson, J. F. (1968), *J. Gen. Microbiol.* 54, 307–317).

*Saccharomyces cerevisiae* is therefore unable to salvage thymidine and may also lack any thymidine phosphorylase activity. *Saccharomyces cerevisiae* is a preferred organism for the heterologous expression of thymidine phosphorylase since the heterologous protein would not be contaminated with endogenously produced thymidine phosphorylase. To facilitate the expression of thymidine phosphorylase in the yeast *Saccharomyces cerevisiae*, HindIII sites were incorporated at the 5' and 3' ends of the synthetic thymidine phosphorylase DNA. Two double-stranded oligonucleotide adaptors, oligonucleotide duplexes VIII and IX, were prepared by annealing oligonucleotides 49 and 50, and oligonucleotides 51 and 52 respectively:

Oligonucleotide Duplex VIII

```
5'-AGCTTAACCTAATTCTAACAAGCAAAGATGTTATTC     -3'   (oligo 49, SEQ49)

3'-     ATTGGATTAAGATTGTTCGTTTCTACAATAAGAAT-5'    (oligo 50, SEQ50)
```

Oligonucleotide Duplex IX

```
5'-ATCTGAATAAA     -3' (oligo 51, SEQ51)

3'-TAGACTTATTTTCGA-5'  oligo 52, SEQ52)
```

These two adaptors and the 1.315 kbp DdeI-EcoRV synthetic thymidine phosphorylase DNA sequence from plasmid pDTPI were ligated into the *Saccharomyces cerevisiae* expression vector pDBP6 (EP 424 117), linearised with HindIII, to generate plasmid pDTP5, FIG. 8. The expression vector pAYE335 was constructed as follows. A 1.434 kbp HindIII-EcoRI DNA fragment containing the protease B promoter was cloned into the polylinker of the M13 bacteriophage mp18 (Yanish-Perron et al (1985) *Gene* 33, 103–119), generating plasmid pAYE333 FIG. 9. Plasmid pAYE333 was linearised by partial digestion with SnaBI and the double stranded oligonucleotide duplex X inserted by ligation at the SnaBI site within the PRB1 promoter.

Oligonucleotide Duplex X

```
5'-GCGGCCGC-3'    oligonucleotide 56

3'-CGCCGGCG-5' oligonucleotide 57
```

Oligonucleotide sequences 56 and 57 are the same. This generates a NotI restriction site at the 5' end of the protease B promoter. The promoter element was further modified by site directed mutagenesis (oligonucleotide direct in vitro mutagenesis system-Version 2, Amersham) according to the manufacturer's instructions. Mutagenesis with the 31-mer oligonucleotide

```
5'-CGCCAATAAAAAAACAAGCTTAACCTAATTC-3'  (oligo 58,
                                        SEQ53)
``` introduces a HindIII restriction site close to the ATG translation initiation codon:

```
CGCCAATAAAAAAACAAACTAAACCTAATTCTAACAAGCAAAGATG
```

```
                                              -continued
unmodified  |  |             Met
(oligo 59, SEQ54)|  |
                 *  *

CGCCAATAAAAAAACAAGCTTAACCTAATTCTAACAAGCAAAGATG
modified   |____|            Met
(oligo 60, SEQ55) HindIII
```

Plasmid pAAH5 (Goodey et al 1987: In *Yeast Biotechnology*, 401–429, Edited by Berry, D. R., Russell, I, and Stewart, G. G. Published by Allen and Unwin) was linearised by partially digesting with BamHI. The 5' protruding ends were blunt-ended with T4 DNA polymerase and dNTPs and ligated with the double-stranded oligonucleotide duplex X. A recombinant plasmid pAYE334 (FIG. 10) was selected in which a NotI restriction site had replaced the BamHI site at the 3' end of the ADHI terminator.

Plasmid pAT153 (Twigg & Sherratt (1980) *Nature* 283, 216–218) was digested with EcoRI/BamHI and the larger 3.36 kbp DNA fragment purified. The 5' protruding ends were blunt-ended with T4 DNA polymerase and dNTPs and recircularised with the double-stranded oligonucleotide duplex X, generating plasmid pAYE328 (FIG. 11).

The 0.8 kbp NotI-HindIII modified protease B promoter sequence was placed upstream of the 0.45 kbp HindIII-NotI ADHI transcription terminator on the pAT153 based plasmid pAYE328 to generate pAYE335 (FIG. 12).

The large 6.38 kbp HindIII-BamHI fragment from the yeast *E. coli* shuttle vector pJDB207 (Beggs, J. D. 1981 *Molecular Genetics in Yeast*, Alfred Benzon Symposium 16, 383–395) was treated with the Klenow fragment of *E. coli* DNA polymerase to create flush ends and ligated with the double stranded oligonucleotide duplex X to generate plasmid pDBP5 (FIG. 13). The 1.25 kbp NotI Protease B promoter/ADH1 terminator cassette from plasmid pAYE335 (FIG. 12) was introduced into the unique NotI site of plasmid pDBP5 generating pDBP6 (FIG. 14).

Transcription initiation and termination sequences are provided by the PRB1 promoter and ADH1 terminator respectively. The thymidine phosphorylase expression plasmid was introduced into the *Saccharomyces cerevisiae* strain DS569 (MATa, leu2) pSAC3 (EP 424 117), by the method described by Beggs, J. D. (1978) *Nature* 275, 104–109. Transformants were selected on a minimal medium lacking leucine (0.15% (w/v) yeast nitrogen base without amino acids and ammonium sulfate (Difco), 5% (w/v) ammonium sulfate, 0.1M citric acid/$Na_2HP_4$, $12H_2O$ pH6.5, 2% (w/v) sucrose). Transformants were grown for 72 hours at 30° C., 200 rpm in 2000 ml flasks containing either 1000 ml of complex (YEP, 1% (w/v) yeast extract, 2% (w/v) bactopeptone and 2% (w/v) sucrose), or defined (0.15% (w/v) yeast nitrogen base without amino acids and ammonium sulfate (Difco), 0.5% (w/v) ammonium sulfate, 0.1M citric acid/$Na_2HPO_4$ $12H_2O$ pH6.5, 2% (w/v) sucrose) liquid medium.

Thymidine phosphorylase was purified from *Escherichia coli* as described by Cook, W. et al (1987) *J. Biol. Chem.* 262, 3788–3789. Thymidine phosphorylase was purified from mammalian cells by disrupting the cells as described previously (Desgranges, C. et al (1981) *Biochim. Biophys. Acta.* 654, 211–218), and the enzyme purified as described by Cook et al (1987) *J. Biol. Chem.* 262, 3788–3789. Thymidine phosphorylase was purified from *Saccharomyces* cerevisiae by centrifuging the culture and resuspending the culture in an equal volume per weight of 50 mM Tris/HCl pH7.6. Cells were lysed by vortexing after the addition of glass beads (40 mesh). The soluble proteins were harvested by centrifugation and the thymidine phosphorylase purified as described by Cook et al (1987) *J. Biol. Chem.* 262, 3788–3789.

The thymidine phosphorylase activity of the purified *E. coli* enzyme was determined spectrophotometrically, relying on the thousand-fold difference in the molar extinction co-efficients of thymidine and thymine. Saturating amounts of thymidine (1 mM) and $KH_2PO_4$ (0.2M), pH 7.4 were combined in a suitable 1 ml reaction tube with 0.1–5 μg/ml *E. coli* thymidine phosphorylase or 1–50 μg/ml human thymidine phosphorylase (purified according to Desgranges et al., 1981), respectively, and the reaction at 25° C. was followed by monitoring the decrease in absorbance at 290 nm. A decrease in absorbance of 1 corresponds to the conversion of a 1 mM solution of thymidine to thymine, thus the decrease in absorbance can be used to calculate the $V_{max}$ of the enzyme ($\mu$moles min$^{-1}$mg$^{-1}$). The results are given in the following table:

| Enzyme | $V_{max}$ ($\mu$moles min$^{-1}$ mg$^{-1}$) |
| --- | --- |
| *E. coli* thymidine phosphorylase | 210 |
| Human thymidine phosphorylase | 10 |

Thus, it can be seen that the *E. coli* thymidine phosphorylase possesses a $V_{max}$ at least 20 fold higher than the human exzyme.

EXAMPLE 3

Expression of Three Thymidine Phosphorylase Domains

Two double-stranded oligonucleotide adaptors, oligonucleotide duplexes XI and XII, were prepared by annealing oligonucleotides 61 and 62, and oligonucleotides 63 and 64 respectively:
Oligonucleotide Duplex XI

```
Oligonucleotide duplex XI:
5'-AGCTTAACCTAATTCTAACAAGCAAAGATGGGTCCAATTG    -3'              (Oligo 61, SEQ56)

3'-      ATTGGATTAAGATTGTTCGTTTCTACCCAGGTTAACAGCT-5'            (Oligo 62, SEQ57)

Oligonucleotide duplex XII:
5'-  CGTTGGTGTTGCTAACGGTGCTGGTGTTAGAACTACTGCTTTATTAACTGATTAAA    -3'  (Oligo 63, SEQ58)

3'-TAGCAACCACAACGATTGCCACGACCACAATCTTGATGACGAAATAATTGACTAATTTTCGA-5' (Oligo 54, SEQ59)
```

To facilitate expression of a domain comprising amino acids 1–241, oligonucleotide duplexes VIII and XII and the 0.66 kbp DdeI-PvuI synthetic thymidine phosphorylase DNA sequence from plasmid pDTP1 were ligated into the *Saccharomyces cerevisiae* expression vector pDBP6 (EP 424 117), linearised with HindIII, to generate plasmid pDTP6 (FIG. 15). To facilitate expression of a domain comprising amino acids 79–241 oligonucleotide duplexes XI and XII, and the 0.42 kbp SalI-PvuI synthetic thymidine phosphorylase DNA sequence from plasmid pDTP1 were likewise ligated into the *Saccharomyces cerevisiae* expression vector pDB6 to generate plasmid pDTP7 (FIG. 16). To facilitate expression of a domain comprising amino acids 79–440, oligonucleotide duplexes XI and IX and the 1.07 kbp SalI-EcoRV synthetic thymidine phosphorylase DNA sequence from plasmid pDTP1 were likewise ligated into vector pDB6 to generate plasmid pDTP8 (FIG. 17). Transcription initiation and termination sequences are provided by the PRB1 promoter and ADH1 terminator respectively. Plasmids pDTP6, pDTP7 and pDTP8 were independently introduced into the *Saccharomyces cerevisiae* strain DS569 and cultured as described above.

EXAMPLE 4

Cloning of Thymidine Phosphorylase From Other Organisms

This can be achieved by designing degenerate single-stranded oligonucleotides based upon the *Escherichia coli* thymidine phosphorylase amino acid sequence. The preferred regions are amino acids 82–91; 110–133 and 171–196, based on the amino acid sequence described in FIG. 1. Within these regions, degenerate DNA sequences can be generated that will encode the amino acids from this region (FIGS. 18A to 18C). From these six degenerate DNA sequences, oligonucleotides can be designed that are greater than 10 base pairs in length and have the lowest degeneracy, for example:

```
From domain 82-92
    5'-GTNGAYAARCAYWS-3'       SEQ 60

3'-CANCTRTTYGTRWS-5'   SEQ 61

From domain 110-133
    5'-CCNATGATHWSNGG-3'       SEQ 62

3'-GGNTACTADWSNCC-5'   SEQ 63

From domain 171-196
    5'-MGNGAYATHACNGC-3'       SEQ 64

3'-KCNCTRTADTGNCG-5'   SEQ 65
```

These single-stranded DNA primers can be used to amplify regions of the thymidine phosphorylase gene from a number of different species by the polymerase chain reaction (PCR). If the organism is prokaryotic, the PCR amplification can be performed on the genomic DNA according to the manufacturer's instruction (GeneAmp, Perkin Elmer Cetus). However, if the organism is eukaryotic, then the PCR amplification should preferably be performed on total RNA or mRNA from the desired species. This can be achieved by reverse transcribing the mRNA into cDNA/RNA hybrid. This can then be used as a template for PCR amplification according to the manufacturer's instructions (RNA PCR, Perkin Elmer Cetus).

The primers (SEQ60–SEQ65) should be used in pairs, SEQ60 with SEQ63 or 65; SEQ62 with SEQ61 or 65; SEQ64 with SEQ61 or 63; SEQ61 with SEQ62 or 64; SEQ63 with SEQ60 or 64; and SEQ65 with SEQ60 or 62.

The PCR amplification cycle conditions should be set to maximise the amplification of the desired product. For example, 94° C. for 1 min; 37° C. for 2 min, 74° C. for 3 min, 40 cycles of amplification, extending the 74° C. incubation by 10 seconds every cycle. Alternatively, to reduce spurious priming during gene amplification, touchdown PCR methodologies can be employed, as described in Don et al (1991) *Nucleic Acids Research* 19, 4008. Briefly, this procedure employs one relatively stringent annealing temperature (eg 55° C.) which is reduced by 1° C. per cycle for the first 10 cycles of amplification. The final annealing temperature would then be 45° C. This annealing temperature is then maintained for another 20 to 25 cycles while the amplification portion of the cycle (72° C. for 3 min) is extended by 10 seconds per cycle.

The PCR amplification product can be blunt-ended with the Klenow fragment of *Escherichia coli* DNA polymerase and cloned into the SmaI site of pUC19. *E. coli* can be transformed to ampicillin resistance with the PCR/pUC19 ligation and transformants containing the thymidine phosphorylase DNA or cDNA sequence identified by DNA sequencing. Such a sequence can be used as a hybridization probe to identify and clone the full length thymidine phosphorylase gene and/or cDNA from appropriate libraries. The full length thymidine phosphorylase gene or cDNA can then be tailored for expression from any one of the expression vectors described in Example 1.

A full length thymidine phosphorylase DNA clone (cDNA or genomic) can also be identified by standard hybridization techniques using 5' $^{32}$P end labelled oligonucleotides. These oligonucleotides can be the sequences described earlier, namely SEQ60–65. These are firstly end labelled with [$\gamma$-$^{32}$P]ATP and T4 polynucleotide kinase and then used as probes to identify potential thymidine phosphorylase genomic or cDNA clones from within appropriate genomic/cDNA libraries prepared in phage or plasmid vectors. Once identified, the thymidine phosphorylase gene or cDNA can be tailored for expression as before.

EXAMPLE 5

Thymidine Phosphorylase Stimulates Endothelial Cell Proliferation

HUVE cells were supplied by the American Type Culture Collection (ATCC number CRL1730). Reagents were supplied by Sigma Chemical Co Ltd unless otherwise stated. Routine HUVE cell cultivation was performed in M199 containing Earle's salts and sodium bicarbonate, 20% (v/v) Foetal Bovine Serum (FBS), 2 mM L-glutamine, 90 µg/ml endothelial cell growth supplement and 100 µg/ml heparin. HUVE cells were maintained in tissue culture flasks (Falcon) coated with type I collagen from calf skin, crosslinked with 1-cyclohexyl-3-(2-morpholinoethyl)-carbodiimide-metho-p-toluene sulfonate (Macklis et al (1985) *In Vitro* 21, 189–194). HUVE cells were grown at 36.5° C., 5% $CO_2$ in a LEEC humidified incubator.

HUVE cells were subcultured at a ratio of 1:3 whenever confluent, cells being disassociated using a 0.5 gl$^{-1}$ trypsin, 0.2 gl$^{-1}$ EDTA solution in $Ca^{2+}/Mg^{2+}$ free Dulbecco's phosphate buffered saline (DPBS) (0.2 gl$^{-1}$ KCl, 0.2 gl$^{-1}$ $KH_2PO_4$, 8 gl$^{-1}$ NaCl, 1.15 gl$^{-1}$ $Na_2HPO_4$). There was no evidence of transformation or loss of the endothelial morphology under these conditions.

A confluent HUVE cell monolayer was trypsinized, washed and resuspended in M199 (including 2 mM L-glutamine and 20% (v/v) FBS). Duplicate haemocytometer counts were made and the cells were diluted to $4\times10^4$ cells/ml M199 (containing 2 mM L-glutamine and 20% (v/v) FBS). A collagen-coated cluster plate (24 flat bottomed 16 mm diameter wells, Costar) was seeded with approximately $2\times10^4$ cells/well (0.5 ml/well) and incubated for 8 hours at 36.5° C. in an atmosphere which included 5% $CO_2$ to allow cell attachment and growth factor depletion. *Escherichia coli* thymidine phosphorylase was added to the wells and cells were incubated for another 18 hours. Sterile [6-$^3$H]-thymidine (1.0 µCi/well, 29 Ci/mmol, Amersham International plc) diluted to 10 µl with DPBS was added and the cells were incubated for a further 4 hours. The medium was discarded, the cells washed gently with 3 ml DPBS and the DNA was fixed with 0.5 ml 5% w/v trichloroacetic acid (20 min, ice cold). The trichloroacetic acid was discarded, the wells were washed with 3 ml Milli-Q water and the DNA was solubilised with 0.3 ml 1M sodium hydroxide (20 min, room temperature, gentle agitation), neutralised with 0.3 ml 1M hydrochloric acid and then transferred to vials containing 10 ml scintillation fluid (Aqualuma, Lumac). The tritium radioactivity was measured by liquid scintillation counting (10 min/vial) using a Packard Tri-Carb 1500 liquid scintillation analyser (FIG. 19).

Thymidine phosphorylase stimulates [$^3$H]-thymidine incorporation by HUVE cells. A bell-shaped dose-response curve was derived, with maximal stimulation being observed around 40 ng/ml. Thymidine phosphorylase is therefore mitogenic towards endothelial cells.

The effect of *E. coli* thymidine phosphorylase addition on endothelial cell proliferation was determined over an eight day period by the acid phosphatase assay for endothelial cell number, Connolly et al (1986) *Anal. Biochem.* 152, 136–140. CPAE cells were maintained as previously described by Finnis et al (1992) *Yeast* 8, 57–60. Cluster plates (24 flat bottomed, 16 mm diameter wells, Costar) were seeded with CPAE cells ($10^4$ per well) in 0.5 ml minimal essential medium containing 2% heat inactivated (65° C., 30 min) dialysed (1 kDa cut-off) FBS, 100 µM thymidine, non-essential amino acids and antibiotics. *E. coli* thymidine phosphorylase in 10 µl DPBS was added to each well to achieve a final concentration of 100 ng/ml. Cells were grown at 36.5° C. in an atmosphere which included 5% $CO_2$ in a humidified incubator. To determine endothelial cell number, the culture medium was discarded and the cells were washed with 1 ml DPBS. Cells were then incubated for 2 hours with a medium containing 0.5 ml 10 mM p-nitrophenyl phosphate (SIGMA 104), 0.1% (v/v) Triton X-100 and 0.1M sodium acetate pH5.5, and the reaction was stopped by the addition of 50 µl 1M sodium hydroxide. The absorbance at 405 nm minus the absorbance at 620 nm ($A_{405}$–$A_{620}$) was determined for each well in the absence of cells and subtracted from the $A_{405}$–$A_{620}$ in the presence of cells (FIG. 20). In the absence of thymidine phosphorylase, cell number, as indicated by the corrected absorbance, declines. However, in the presence of 100 ng/ml thymidine phosphorylase, the cell number increases.

EXAMPLE 6

Expression of a Fusion of Thymidine Phosphorylase and Antibody Region

Thymidine phosphorylase, or a functional portion thereof, can be expressed as a fusion protein with a functional variable-region of a monoclonal antibody which will direct the thymidine phosphorylase to the chosen location. Total RNA is prepared from $1\times10^8$ hybridoma cells expressing the desired monoclonal antibody. Total RNA was used for first strand cDNA synthesis using Moloney murine leukaemia virus reverse transcriptase and random primers at 37° C. for 1 hour as described by Chaudhary, V. et al (1990) *PNAS* 87, 1066–1070. The variable light ($V_L$) and ($V_H$) regions of the antibody cDNA were amplified by polymerase chain reaction (PCR) using primers ($V_L$-5', $V_L$-3', $V_H$-5' and $V_H$-3') and conditions described by Chaudhary, V. et al (1990, see above). The $V_L$ and $V_H$ cDNA segments, when ligated in the order 5'-$V_L$-$V_H$-3', are linked by a short peptide linker region. By using appropriate double-stranded oligonucleotide linkers, this functional antibody variable region can be cloned upstream of the synthetic thymidine phosphorylase described in FIGS. 1 and 4 to 4E. The DNA insert encoding the $V_L$-$V_H$-thymidine fusion protein was inserted into the HindIII site of pDBP6 (FIG. 14) with the aid of suitable double-stranded oligonucleotide linkers. The $V_L$-$V_H$-thymidine phosphorylase fusion protein can then be expressed from the *S. cerevisiae* PRB1 promoter unless the expression vector is used to transform a suitable host strain, such as DS569 (MATa, leu2) pSAC3 (EP 424 117). Transformants were selected and cultured as described in Example 2.

EXAMPLE 7

Conjugation

This example illustrates how thymidine phosphorylase, or a functional portion thereof, can be conjugated to antibodies by various coupling/cross-linking reagents. This methodology equally applies to the coupling of thymidine phosphorylase to any other protein which would act as a ligand to target thymidine phosphorylase.

1 mg of antibody in 0.5 ml 30 mM HEPES pH7.4 was reacted with 50 µl sulfo-SMCC at 50 mg/ml in 30 mM HEPES pH7.4 (Pierce) for 30 min at 4° C. The sulfhydryl reactive antibody was isolated by dialysis into 30 mM HEPES pH7.4. 1 mg thymidine phosphorylase in 0.5 ml in degassed 30 mM HEPES pH7.4, 1 mM EDTA, was then reacted with the activated antibody at 4° C. for 5 min. The thymidine phosphorylase antibody conjugate was isolated by gel filtration.

This same procedure can be employed to cross-link thymidine phosphorylase and antibodies if sulfo-MBS is employed as the cross-linking group instead of sulfo-SMCC.

SMCC or MBS (Pierce) can also be used as the cross-linking group instead of sulfo-SMCC or sulfo-MBS, in which case the SMCC or MBS should be dissolved in DMSO before use.

Thus, 1.5 mg MBS or SMCC was dissolved in 50 µl DMSO. 0.5 mg of thymidine phosphorylase and 0.5 mg of the antibody were added to phosphate buffered saline pH6.0 to a final concentration of 1 mg/ml and mixed in a 10 ml conical flask at 22° C. The MBS or SMCC solution was added to the protein solution and shaken for a further 30 minutes at 22° C. The derivatized protein was desalted by FPLC using a G25 superfine column into PBS pH7.4. Peak fractions were pooled.

Where necessary, free sulfhydryl groups on the antibody can be blocked with N-ethyl-maleimide and primary amines on the thymidine phosphorylase moiety can be modified by Trant's Reagent (Pierce) to introduce sulfhydryl groups allowing coupling to the activated antibody. Using the same cross-linking the thymidine phosphorylase moiety first as described above and then cross-link the sulfhydryl groups on the targeting ligand, for example the antibody.

Thymidine phosphorylase or a functional portion thereof can also be conjugated to synthetic carbohydrates with the Lewis-X or sialyl Lewis-X determinant, FIGS. 21A and 21B, or purified natural carbohydrates containing this determinant, eg LNFIII (Calbiochem) by procedures involving chemical spacers like p-aminophenyl, aminophenylethyl and acetyl phenylenediamine as described by Berg, E. et al (1991) *J. Biol. Chem.* 266, 14869–14872.

EXAMPLE 8

Formulation of an Agent with Thymidine Phosphorylase Activity

Thymidine phosphorylase prepared as above was made up as a 0.01% w/v solution in water-for-injection containing 4.5% w/v human albumin, for injection into a vein adjacent an ulcer or other target site. Alternatively, the thymidine phosphorylase, made up as a 0.01% (w/v) solution in water-for-injection, can be applied to the target site in the form of an aerosol.

EXAMPLE 9

Bioactive Graft

Thymidine phosphorylase was cross-linked to Dacron vascular prosthetic grafts and human-albumin-coated Dacron grafts, (Hake, V. et al (1991) *Thorac. Cardiovasc. Surgeon* 39, 208–213). This procedure enhances the rate of endothelial cell growth and hence reduces the time taken to form a confluent endothelium. Thymidine phosphorylase at 2 mg/ml in 30 mM HEPES pH7.4 was reacted with sulfo-SMCC 50 mg/ml in 30 mM HEPES pH7.4 for 30 min at 4° C. in the presence of the vascular prostheses. The thymidine phosphorylase conjugated vascular prostheses were then implanted as required.

We claim:

1. A method of modulating cellular proliferation in a mammal in need thereof which comprises administering to said mammal an amount of a pharmaceutical composition effective to modulate cellular proliferation, said composition comprising a pharmaceutically acceptable vehicle and a non-human thymidine phosphorylase polypeptide characterized by having a thymidine phosphorylase activity at least about 5% of native E. coli thymidine phosphorylase, wherein said activity is determined as the $V_{max}$(μmoles min$^{-1}$mg$^{-1}$) of the enzyme at 25° C. in the presence of 1 mM thymidine in 0.2M $KH_2PO_4$ at pH 7.4.

2. A method in accordance with claim 1, wherein said polypeptide is characterized by having a thymidine phosphorylase activity at least about 50% of native E. coli thymidine phosphorylase.

3. A method in accordance with claim 1, wherein said polypeptide is characterized by having a thymidine phosphorylase activity at least about 90% of native E. coli thymidine phosphorylase.

4. A method in accordance with claim 1, wherein said polypeptide is native E. coli thymidine phosphorylase, or a functional portion thereof.

5. A method in accordance with claim 1, wherein the administration of said polypeptide to said mammal causes healing of a wound by increasing cellular proliferation at said wound.

6. A method in accordance with claim 5, wherein said polypeptide is characterized by having a thymidine phosphorylase activity at least about 50% of native E. coli thymidine phosphorylase.

7. A method in accordance with claim 5, wherein said polypeptide is characterized by having a thymidine phosphorylase activity at least about 90% of native E. coli thymidine phosphorylase.

8. A method in accordance with claim 5, where said polypeptide is applied topically to said wound.

9. A method in accordance with claim 1, wherein said polypeptide is administered as a conjugate with a targeting agent which causes said polypeptide to be accumulated at the site where modulation of cellular proliferation is required.

10. A method in accordance with claim 9, wherein said targeting agent is a monoclonal antibody.

11. A method in accordance with claim 9, wherein said conjugate is a fusion protein expressed by recombinant techniques in a suitable non-human host.

12. A method in accordance with claim 11, wherein said host is a yeast.

* * * * *

SEQUENCE LISTING (1) GENERAL INFORMATION:

(iii) NUMBER OF SEQUENCES: 76

(2) INFORMATION FOR SEQ ID NO:1:

(i) SEQUENCE CHARACTERISTICS:
      (A) LENGTH: 440 amino acids
      (B) TYPE: amino acid
      (D) TOPOLOGY: linear -continued (ii) MOLECULE TYPE: protein (iii) HYPOTHETICAL: NO (vi) ORIGINAL SOURCE:
         (A) ORGANISM: Escherichia coli
         (B) STRAIN: K12

(ix) FEATURE:
         (A) NAME/KEY: Protein
         (B) LOCATION: 1..440
         (D) OTHER INFORMATION: /note= "Figure 1"

(xi) SEQUENCE DESCRIPTION: SEQ ID NO:1:

```
Leu Phe Leu Ala Gln Glu Ile Ile Arg Lys Lys Arg Asp Gly His Ala
1               5                   10                  15

Leu Ser Asp Glu Glu Ile Arg Phe Phe Ile Asn Gly Ile Arg Asp Asn
                20                  25                  30

Thr Ile Ser Glu Gly Gln Ile Ala Ala Leu Ala Met Thr Ile Phe Phe
            35                  40                  45

His Asp Met Thr Met Pro Glu Arg Val Ser Leu Thr Met Ala Met Arg
    50                  55                  60

Asp Ser Gly Thr Val Leu Asp Trp Lys Ser Leu His Leu Asn Gly Pro
65                  70                  75                  80

Ile Val Asp Lys His Ser Thr Gly Val Gly Asp Val Thr Ser Leu
                85                  90                  95

Met Leu Gly Pro Met Val Ala Ala Cys Gly Gly Tyr Ile Pro Met Ile
                100                 105                 110

Ser Gly Arg Gly Leu Gly His Thr Gly Gly Thr Leu Asp Lys Leu Glu
            115                 120                 125

Ser Ile Pro Gly Phe Asp Ile Phe Pro Asp Asp Asn Arg Phe Arg Glu
        130                 135                 140

Ile Ile Lys Asp Val Gly Val Ala Ile Ile Gly Gln Thr Ser Ser Leu
145                 150                 155                 160

Ala Pro Ala Asp Lys Arg Phe Tyr Ala Thr Arg Asp Ile Thr Ala Thr
                165                 170                 175

Val Asp Ser Ile Pro Leu Ile Thr Ala Ser Ile Leu Ala Lys Lys Leu
            180                 185                 190

Ala Glu Gly Leu Asp Ala Leu Val Met Asp Val Lys Val Gly Ser Gly
        195                 200                 205

Ala Phe Met Pro Thr Tyr Glu Leu Ser Glu Ala Leu Ala Glu Ala Ile
    210                 215                 220

Val Gly Val Ala Asn Gly Ala Gly Val Arg Thr Thr Ala Leu Leu Thr
225                 230                 235                 240

Asp Met Asn Gln Val Leu Ala Ser Ser Ala Gly Asn Ala Val Glu Val
                245                 250                 255

Arg Glu Ala Val Gln Phe Leu Thr Gly Glu Tyr Arg Asn Pro Arg Leu
            260                 265                 270

Phe Asp Val Thr Met Ala Leu Cys Val Glu Met Leu Ile Ser Gly Lys
        275                 280                 285

Leu Ala Lys Asp Asp Ala Glu Ala Arg Ala Lys Leu Gln Ala Val Leu
    290                 295                 300

Asp Asn Gly Lys Ala Ala Glu Val Phe Gly Arg Met Val Ala Ala Gln
305                 310                 315                 320

Lys Gly Pro Thr Asp Phe Val Glu Asn Tyr Ala Lys Tyr Leu Pro Thr
                325                 330                 335
```

```
Ala Met Leu Thr Lys Ala Val Tyr Ala Asp Thr Glu Gly Phe Val Ser
            340                 345                 350

Glu Met Asp Thr Arg Ala Leu Gly Met Ala Val Val Ala Met Gly Gly
            355                 360                 365

Gly Arg Arg Gln Ala Ser Asp Thr Ile Asp Tyr Ser Val Gly Phe Thr
            370                 375                 380

Asp Met Ala Arg Leu Gly Asp Gln Val Asp Gly Gln Arg Pro Leu Ala
385                 390                 395                 400

Val Ile His Ala Lys Asp Glu Asn Asn Trp Gln Glu Ala Ala Lys Ala
            405                 410                 415

Val Lys Ala Ala Ile Lys Leu Ala Asp Lys Ala Pro Glu Ser Thr Pro
            420                 425                 430

Thr Val Tyr Arg Arg Ile Ser Glu
            435                 440
```

(2) INFORMATION FOR SEQ ID NO:2:

(i) SEQUENCE CHARACTERISTICS:
        (A) LENGTH: 71 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..71
        (D) OTHER INFORMATION: /function= "oligonucleotide 1"

(xi) SEQUENCE DESCRIPTION: SEQ ID NO:2:

```
CTTAGCTCAA GAAATTATTA GAAAAAAAG AGATGGTCAT GCTTTATCTG ATGAAGAAAT      60

TAGATTCTTC A                                                         71
```

(2) INFORMATION FOR SEQ ID NO:3:

(i) SEQUENCE CHARACTERISTICS:
        (A) LENGTH: 71 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..71
        (D) OTHER INFORMATION: /function= "oligonucleotide 2"

(xi) SEQUENCE DESCRIPTION: SEQ ID NO:3:

```
TTAACGGTAT TAGAGATAAC ACTATTTCTG AAGGTCAAAT TGCTGCTTTA GCTATGACTA      60

TTTTCTTCCA T                                                         71
```

(2) INFORMATION FOR SEQ ID NO:4:

(i) SEQUENCE CHARACTERISTICS:
        (A) LENGTH: 70 base pairs
        (B) TYPE: nucleic acid (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..70
        (D) OTHER INFORMATION: /function= "oligonucleotide 3"

(xi) SEQUENCE DESCRIPTION: SEQ ID NO:4:

GATATGACTA TGCCAGAAAG AGTTTCTTTA ACTATGGCTA TGAGAGATTC TGGTACTGTT    60

TTAGATTGGA                                                          70

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..27
        (D) OTHER INFORMATION: /function= "oligonucleotide 4"

(xi) SEQUENCE DESCRIPTION: SEQ ID NO:5:

AATCTTTACA TTTAAACGGT CCAATTG                                       27

(2) INFORMATION FOR SEQ ID NO:6:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..42
        (D) OTHER INFORMATION: /function= "oligonucleotide 5"

(xi) SEQUENCE DESCRIPTION: SEQ ID NO:6:

TCGACAATTG GACCGTTTAA ATGTAAAGAT TCCAATCTA AA                       42

(2) INFORMATION FOR SEQ ID NO:7:

(i) SEQUENCE CHARACTERISTICS:
        (A) LENGTH: 70 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
    (A) NAME/KEY: misc_feature
    (B) LOCATION: 1..70
    (D) OTHER INFORMATION: /function= "oligonucleotide 6"

(xi) SEQUENCE DESCRIPTION: SEQ ID NO:7:

```
ACAGTACCAG AATCTCTCAT AGCCATAGTT AAAGAAACTC TTTCTGGCAT AGTCATATCA      60

TGGAAGAAAA                                                            70
```

(2) INFORMATION FOR SEQ ID NO:8:

(i) SEQUENCE CHARACTERISTICS:
    (A) LENGTH: 70 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (iv) ANTI-SENSE: NO (ix) FEATURE:
    (A) NAME/KEY: misc_feature
    (B) LOCATION: 1..70
    (D) OTHER INFORMATION: /function= "oligonucleotide 7"

(xi) SEQUENCE DESCRIPTION: SEQ ID NO:8:

```
TAGTCATAGC TAAAGCAGCA ATTTGACCTT CAGAAATAGT GTTATCTCTA ATACCGTTAA      60

TGAAGAATCT                                                            70
```

(2) INFORMATION FOR SEQ ID NO:9:

(i) SEQUENCE CHARACTERISTICS:
    (A) LENGTH: 61 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (iv) ANTI-SENSE: NO (ix) FEATURE:
    (A) NAME/KEY: misc_feature
    (B) LOCATION: 1..61
    (D) OTHER INFORMATION: /function= "oligonucleotide 8"

(xi) SEQUENCE DESCRIPTION: SEQ ID NO:9:

```
AATTTCTTCA TCAGATAAAG CATGACCATC TCTTTTTTTT CTAATAATTT CTTGAGCTAA      60

G                                                                     61
```

(2) INFORMATION FOR SEQ ID NO:10:

(i) SEQUENCE CHARACTERISTICS:
    (A) LENGTH: 73 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (iv) ANTI-SENSE: NO (ix) FEATURE:
            (A) NAME/KEY: misc_feature
            (B) LOCATION: 1..73
            (D) OTHER INFORMATION: /function= "oligonucleotide 9"

(xi) SEQUENCE DESCRIPTION: SEQ ID NO:10:

TCGACAAACA TTCTACTGGT GGTGTTGGTG ATGTTACTTC TTTAATGTTA GGTCCAATGG      60

TTGCTGCTTG TGG                                                        73

(2) INFORMATION FOR SEQ ID NO:11:

(i) SEQUENCE CHARACTERISTICS:
        (A) LENGTH: 70 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..70
        (D) OTHER INFORMATION: /function= "oligonucleotide 10"

(xi) SEQUENCE DESCRIPTION: SEQ ID NO:11:

TGGTTACATT CCAATGATTT CTGGTAGAGG TTTAGGTCAT ACTGGTGGTA CTTTAGATAA      60

ATTAGAATCT                                                            70

(2) INFORMATION FOR SEQ ID NO:12:

(i) SEQUENCE CHARACTERISTICS:
        (A) LENGTH: 70 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..70
        (D) OTHER INFORMATION: /function= "oligonucleotide 11"

(xi) SEQUENCE DESCRIPTION: SEQ ID NO:12:

ATTCCAGGTT TCGATATTTT CCCAGATGAT AACAGATTCA GAGAAATTAT TAAAGATGTT      60

GGTGTTGCTA                                                            70

(2) INFORMATION FOR SEQ ID NO:13:

(i) SEQUENCE CHARACTERISTICS:
        (A) LENGTH: 70 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
             (A) NAME/KEY: misc_feature
             (B) LOCATION: 1..70
             (D) OTHER INFORMATION: /function= "oligonucleotide 12"

(xi) SEQUENCE DESCRIPTION: SEQ ID NO:13:

TTATTGGTCA AACTTCTTCT TTAGCTCCAG CTGATAAAAG ATTCTACGCT ACTAGAGATA      60

TTACTGCTAC                                                            70

(2) INFORMATION FOR SEQ ID NO:14:

(i) SEQUENCE CHARACTERISTICS:
            (A) LENGTH: 70 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (ix) FEATURE:
             (A) NAME/KEY: misc_feature
             (B) LOCATION: 1..70
             (D) OTHER INFORMATION: /function= "oligonucleotide 13"

(xi) SEQUENCE DESCRIPTION: SEQ ID NO:14:

TGTTGATTCT ATTCCATTAA TTACTGCTTC TATTTTAGCT AAAAAATTAG CTGAAGGTTT      60

AGATGCTTTA                                                            70

(2) INFORMATION FOR SEQ ID NO:15:

(i) SEQUENCE CHARACTERISTICS:
            (A) LENGTH: 74 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (ix) FEATURE:
             (A) NAME/KEY: misc_feature
             (B) LOCATION: 1..74
             (D) OTHER INFORMATION: /function= "oligonucleotide 14"

(xi) SEQUENCE DESCRIPTION: SEQ ID NO:15:

GTTATGGATG TTAAAGTTGG TTCTGGTGCT TTCATGCCAA CTTACGAATT ATCTGAAGCC      60

TTGGCTGAAG CGAT                                                       74

(2) INFORMATION FOR SEQ ID NO:16:

(i) SEQUENCE CHARACTERISTICS:
            (A) LENGTH: 62 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (ix) FEATURE:
              (A) NAME/KEY: misc_feature
              (B) LOCATION: 1..62
              (D) OTHER INFORMATION: /function= "oligonucleotide 15"

(xi) SEQUENCE DESCRIPTION: SEQ ID NO:16:

CGCTTCAGCC AAGGCTTCAG ATAATTCGTA AGTTGGCATG AAAGCACCAG AACCAACTTT        60

AA                                                                      62

(2) INFORMATION FOR SEQ ID NO:17:

(i) SEQUENCE CHARACTERISTICS:
              (A) LENGTH: 70 base pairs
              (B) TYPE: nucleic acid
              (C) STRANDEDNESS: double
              (D) TOPOLOGY: linear (ii) MOLECULE TYPE: cDNA (iii) HYPOTHETICAL: NO (iv) ANTI-SENSE: NO (ix) FEATURE:
              (A) NAME/KEY: misc_feature
              (B) LOCATION: 1..70
              (D) OTHER INFORMATION: /function= "oligonucleotide 16"

(xi) SEQUENCE DESCRIPTION: SEQ ID NO:17:

CATCCATAAC TAAAGCATCT AAACCTTCAG CTAATTTTTT AGCTAAAATA GAAGCAGTAA        60

TTAATGGAAT                                                              70

(2) INFORMATION FOR SEQ ID NO:18:

(i) SEQUENCE CHARACTERISTICS:
              (A) LENGTH: 70 base pairs
              (B) TYPE: nucleic acid
              (C) STRANDEDNESS: double
              (D) TOPOLOGY: linear (ii) MOLECULE TYPE: cDNA (iii) HYPOTHETICAL: NO (iv) ANTI-SENSE: NO (ix) FEATURE:
              (A) NAME/KEY: misc_feature
              (B) LOCATION: 1..70
              (D) OTHER INFORMATION: /function= "oligonucleotide 17"

(xi) SEQUENCE DESCRIPTION: SEQ ID NO:18:

AGAATCAACA GTAGCAGTAA TATCTCTAGT AGCGTAGAAT CTTTTATCAG CTGGAGCTAA        60

AGAAGAAGTT                                                              70

(2) INFORMATION FOR SEQ ID NO:19:

(i) SEQUENCE CHARACTERISTICS:
              (A) LENGTH: 70 base pairs
              (B) TYPE: nucleic acid
              (C) STRANDEDNESS: double
              (D) TOPOLOGY: linear (ii) MOLECULE TYPE: cDNA (iii) HYPOTHETICAL: NO (iv) ANTI-SENSE: NO (ix) FEATURE:
            (A) NAME/KEY: misc_feature
            (B) LOCATION: 1..70
            (D) OTHER INFORMATION: /function= "oligonucleotide 18"

(xi) SEQUENCE DESCRIPTION: SEQ ID NO:19:

TGACCAATAA TAGCAACACC AACATCTTTA ATAATTTCTC TGAATCTGTT ATCATCTGGG     60

AAAATATCGA                                                            70

(2) INFORMATION FOR SEQ ID NO:20:

(i) SEQUENCE CHARACTERISTICS:
            (A) LENGTH: 70 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY: misc_feature
            (B) LOCATION: 1..70
            (D) OTHER INFORMATION: /function= "oligonucleotide 19"

(xi) SEQUENCE DESCRIPTION: SEQ ID NO:20:

AACCTGGAAT AGATTCTAAT TTATCTAAAG TACCACCAGT ATGACCTAAA CCTCTACCAG     60

AAATCATTGG                                                            70

(2) INFORMATION FOR SEQ ID NO:21:

(i) SEQUENCE CHARACTERISTICS:
            (A) LENGTH: 79 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY: misc_feature
            (B) LOCATION: 1..79
            (D) OTHER INFORMATION: /function= "oligonucleotide 20"

(xi) SEQUENCE DESCRIPTION: SEQ ID NO:21:

AATGTAACCA CCACAAGCAG CAACCATTGG ACCTAACATT AAAGAAGTAA CATCACCAAC     60

ACCACCAGTA GAATGTTTG                                                  79

(2) INFORMATION FOR SEQ ID NO:22:

(i) SEQUENCE CHARACTERISTICS:
            (A) LENGTH: 66 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (ix) FEATURE:

(A) NAME/KEY: misc_feature
                (B) LOCATION: 1..66
                (D) OTHER INFORMATION: /function= "oligonucleotide 21"

(xi) SEQUENCE DESCRIPTION: SEQ ID NO:22:

CGTTGGTGTT GCTAACGGTG CTGGTGTTAG AACTACTGCT TTATTAACTG ATATGAACCA      60

AGTTTT                                                                66

(2) INFORMATION FOR SEQ ID NO:23:

(i) SEQUENCE CHARACTERISTICS:
                (A) LENGTH: 70 base pairs
                (B) TYPE: nucleic acid
                (C) STRANDEDNESS: double
                (D) TOPOLOGY: linear (ii) MOLECULE TYPE: cDNA (iii) HYPOTHETICAL: NO (iv) ANTI-SENSE: NO (ix) FEATURE:
                (A) NAME/KEY: misc_feature
                (B) LOCATION: 1..70
                (D) OTHER INFORMATION: /function= "oligonucleotide 22"

(xi) SEQUENCE DESCRIPTION: SEQ ID NO:23:

AGCTTCTTCT GCTGGTAACG CTGTTGAAGT TAGAGAAGCT GTTCAATTCT TAACTGGTGA      60

ATACAGAAAC                                                            70

(2) INFORMATION FOR SEQ ID NO:24:

(i) SEQUENCE CHARACTERISTICS:
                (A) LENGTH: 70 base pairs
                (B) TYPE: nucleic acid
                (C) STRANDEDNESS: double
                (D) TOPOLOGY: linear (ii) MOLECULE TYPE: cDNA (iii) HYPOTHETICAL: NO (iv) ANTI-SENSE: NO (ix) FEATURE:
                (A) NAME/KEY: misc_feature
                (B) LOCATION: 1..70
                (D) OTHER INFORMATION: /function= "oligonucleotide 23"

(xi) SEQUENCE DESCRIPTION: SEQ ID NO:24:

CCAAGATTAT TCGATGTTAC TATGGCTTTA TGTGTTGAAA TGTTAATTTC TGGTAAATTA      60

GCTAAAGATG                                                            70

(2) INFORMATION FOR SEQ ID NO:25:

(i) SEQUENCE CHARACTERISTICS:
                (A) LENGTH: 70 base pairs
                (B) TYPE: nucleic acid
                (C) STRANDEDNESS: double
                (D) TOPOLOGY: linear (ii) MOLECULE TYPE: cDNA (iii) HYPOTHETICAL: NO (iv) ANTI-SENSE: NO (ix) FEATURE:
                (A) NAME/KEY: misc_feature (B) LOCATION: 1..70
        (D) OTHER INFORMATION: /function= "oligonucleotide 24"

(xi) SEQUENCE DESCRIPTION: SEQ ID NO:25:

ATGCTGAAGC TAGAGCTAAA TTACAAGCTG TTTTAGATAA CGGTAAAGCT GCTGAAGTTT     60

TCGGTAGAAT     70

(2) INFORMATION FOR SEQ ID NO:26:

(i) SEQUENCE CHARACTERISTICS:
        (A) LENGTH: 70 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..70
        (D) OTHER INFORMATION: /function= "oligonucleotide 25"

(xi) SEQUENCE DESCRIPTION: SEQ ID NO:26:

GGTTGCTGCT CAAAAGGTC CAACTGATTT CGTTGAAAAC TACGCTAAAT ACTTACCAAC     60

TGCTATGTTA     70

(2) INFORMATION FOR SEQ ID NO:27:

(i) SEQUENCE CHARACTERISTICS:
        (A) LENGTH: 70 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..70
        (D) OTHER INFORMATION: /function= "oligonucleotide 26"

(xi) SEQUENCE DESCRIPTION: SEQ ID NO:27:

ACTAAAGCTG TTTACGCTGA TACTGAAGGT TTCGTTTCTG AAATGGATAC TAGAGCTTTA     60

GGTATGGCTG     70

(2) INFORMATION FOR SEQ ID NO:28:

(i) SEQUENCE CHARACTERISTICS:
        (A) LENGTH: 70 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..70

(D) OTHER INFORMATION: /function= "oligonucleotide 27"

(xi) SEQUENCE DESCRIPTION: SEQ ID NO:28:

TTGTTGCTAT GGGTGGTGGT AGAAGACAAG CCTCTGATAC TATTGATTAC TCTGTTGGTT    60

TCACTGATAT    70

(2) INFORMATION FOR SEQ ID NO:29:

(i) SEQUENCE CHARACTERISTICS:
      (A) LENGTH: 70 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: misc_feature
      (B) LOCATION: 1..70
      (D) OTHER INFORMATION: /function= "oligonucleotide 28"

(xi) SEQUENCE DESCRIPTION: SEQ ID NO:29:

GGCTAGATTA GGTGATCAAG TTGATGGTCA AAGACCATTA GCTGTTATTC ATGCTAAAGA    60

TGAAAACAAC    70

(2) INFORMATION FOR SEQ ID NO:30:

(i) SEQUENCE CHARACTERISTICS:
      (A) LENGTH: 60 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: misc_feature
      (B) LOCATION: 1..60
      (D) OTHER INFORMATION: /function= "oligonucleotide 29"

(xi) SEQUENCE DESCRIPTION: SEQ ID NO:30:

TGGCAAGAAG CTGCTAAAGC TGTTAAAGCT GCTATTAAAT TAGCTGATAA AGCTCCAGAA    60

(2) INFORMATION FOR SEQ ID NO:31:

(i) SEQUENCE CHARACTERISTICS:
      (A) LENGTH: 29 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: misc_feature
      (B) LOCATION: 1..29
      (D) OTHER INFORMATION: /function= "oligonucleotide 30"

(xi) SEQUENCE DESCRIPTION: SEQ ID NO:31:

TCTACTCCAA CTGTTTACAG AAGGATATC                                              29

(2) INFORMATION FOR SEQ ID NO:32:

(i) SEQUENCE CHARACTERISTICS:
        (A) LENGTH: 40 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..40
        (D) OTHER INFORMATION: /function= "oligonucleotide 31"

(xi) SEQUENCE DESCRIPTION: SEQ ID NO:32:

GATATCCTTC TGTAAACAGT TGGAGTAGAT TCTGGAGCTT                                   40

(2) INFORMATION FOR SEQ ID NO:33:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..60
        (D) OTHER INFORMATION: /function= "oligonucleotide 32"

(xi) SEQUENCE DESCRIPTION: SEQ ID NO:33:

TATCAGCTAA TTTAATAGCA GCTTTAACAG CTTTAGCAGC TTCTTGCCAG TTGTTTTCAT             60

(2) INFORMATION FOR SEQ ID NO:34:

(i) SEQUENCE CHARACTERISTICS:
        (A) LENGTH: 69 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..69
        (D) OTHER INFORMATION: /function= "oligonucleotide 33"

(xi) SEQUENCE DESCRIPTION: SEQ ID NO:34:

CTTTAGCATG AATAACAGCT AATGGTCTTT GACCATCAAC TTGATCACCT AATCTAGCCA             60

TATCAGTGA                                                                    69

(2) INFORMATION FOR SEQ ID NO:35:

```
        (i) SEQUENCE CHARACTERISTICS:
            (A) LENGTH: 71 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY: misc_feature
            (B) LOCATION: 1..71
            (D) OTHER INFORMATION: /function= "oligonucleotide 34"

(xi) SEQUENCE DESCRIPTION: SEQ ID NO:35:

AACCAACAGA GTAATCAATA GTATCAGAGG CTTGTCTTCT ACCACCACCC ATAGCAACAA       60

CAGCCATACC T                                                          71

(2) INFORMATION FOR SEQ ID NO:36:

(i) SEQUENCE CHARACTERISTICS:
            (A) LENGTH: 70 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY: misc_feature
            (B) LOCATION: 1..70
            (D) OTHER INFORMATION: /function= "oligonucleotide 35"

(xi) SEQUENCE DESCRIPTION: SEQ ID NO:36:

AAAGCTCTAG TATCCATTTC AGAAACGAAA CCTTCAGTAT CAGCGTAAAC AGCTTTAGTT       60

AACATAGCAG                                                            70

(2) INFORMATION FOR SEQ ID NO:37:

(i) SEQUENCE CHARACTERISTICS:
            (A) LENGTH: 70 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY: misc_feature
            (B) LOCATION: 1..70
            (D) OTHER INFORMATION: /function= "oligonucleotide 36"

(xi) SEQUENCE DESCRIPTION: SEQ ID NO:37:

TTGGTAAGTA TTTAGCGTAG TTTTCAACGA AATCAGTTGG ACCTTTTTGA GCAGCAACCA       60

TTCTACCGAA                                                            70

(2) INFORMATION FOR SEQ ID NO:38:
```

(i) SEQUENCE CHARACTERISTICS:
            (A) LENGTH: 70 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY: misc_feature
            (B) LOCATION: 1..70
            (D) OTHER INFORMATION: /function= "oligonucleotide 37"

(xi) SEQUENCE DESCRIPTION: SEQ ID NO:38:

AACTTCAGCA GCTTTACCGT TATCTAAAAC AGCTTGTAAT TTAGCTCTAG CTTCAGCATC      60

ATCTTTAGCT                                                            70

(2) INFORMATION FOR SEQ ID NO:39:

(i) SEQUENCE CHARACTERISTICS:
            (A) LENGTH: 69 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY: misc_feature
            (B) LOCATION: 1..69
            (D) OTHER INFORMATION: /function= "oligonucleotide 38"

(xi) SEQUENCE DESCRIPTION: SEQ ID NO:39:

AATTTACCAG AAATTAACAT TTCAACACAT AAAGCCATAG TAACATCGAA TAATCTTGGG      60

TTTCTGTAT                                                             69

(2) INFORMATION FOR SEQ ID NO:40:

(i) SEQUENCE CHARACTERISTICS:
            (A) LENGTH: 71 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY: misc_feature
            (B) LOCATION: 1..71
            (D) OTHER INFORMATION: /function= "oligonucleotide 39"

(xi) SEQUENCE DESCRIPTION: SEQ ID NO:40:

TCACCAGTTA AGAATTGAAC AGCTTCTCTA ACTTCAACAG CGTTACCAGC AGAAGAAGCT      60

AAAACTTGGT T                                                          71

(2) INFORMATION FOR SEQ ID NO:41:

(i) SEQUENCE CHARACTERISTICS:

(A) LENGTH: 57 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..57
        (D) OTHER INFORMATION: /function= "oligonucleotide 40"

(xi) SEQUENCE DESCRIPTION: SEQ ID NO:41:

CATATCAGTT AATAAAGCAG TAGTTCTAAC ACCAGCACCG TTAGCAACAC CAACGAT    57

(2) INFORMATION FOR SEQ ID NO:42:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..10
        (D) OTHER INFORMATION: /function= "oligonucleotide 41"

(xi) SEQUENCE DESCRIPTION: SEQ ID NO:42:

CATGTTATTC    10

(2) INFORMATION FOR SEQ ID NO:43:

(i) SEQUENCE CHARACTERISTICS:
        (A) LENGTH: 11 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..11
        (D) OTHER INFORMATION: /function= "oligonucleotide 43"

(xi) SEQUENCE DESCRIPTION: SEQ ID NO:43:

ATCTGAATAA C    11

(2) INFORMATION FOR SEQ ID NO:44:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
            (A) NAME/KEY: misc_feature
            (B) LOCATION: 1..15
            (D) OTHER INFORMATION: /function= "oligonucleotide 44"

(xi) SEQUENCE DESCRIPTION: SEQ ID NO:44:

CATGGTTATT CAGAT                                                              15

(2) INFORMATION FOR SEQ ID NO:45:

(i) SEQUENCE CHARACTERISTICS:
            (A) LENGTH: 14 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY: misc_feature
            (B) LOCATION: 1..14
            (D) OTHER INFORMATION: /function= "oligonucleotide 45"

(xi) SEQUENCE DESCRIPTION: SEQ ID NO:45:

AATTCATGTT ATTC                                                               14

(2) INFORMATION FOR SEQ ID NO:46:

(i) SEQUENCE CHARACTERISTICS:
            (A) LENGTH: 13 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY: misc_feature
            (B) LOCATION: 1..13
            (D) OTHER INFORMATION: /function= "oligonucleotide 46"

(xi) SEQUENCE DESCRIPTION: SEQ ID NO:46:

TAAGAATAAC ATG                                                                13

(2) INFORMATION FOR SEQ ID NO:47:

(i) SEQUENCE CHARACTERISTICS:
            (A) LENGTH: 11 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY: misc_feature
            (B) LOCATION: 1..11

(D) OTHER INFORMATION: /function= "oligonucleotide 47"

(xi) SEQUENCE DESCRIPTION: SEQ ID NO:47:

ATCTGAATAA G                                                                11

(2) INFORMATION FOR SEQ ID NO:48:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..15
        (D) OTHER INFORMATION: /function= "oligonucleotide 48"

(xi) SEQUENCE DESCRIPTION: SEQ ID NO:48:

AATTCTTATT CAGAT                                                            15

(2) INFORMATION FOR SEQ ID NO:49:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..36
        (D) OTHER INFORMATION: /function= "oligonucleotide 49"

(xi) SEQUENCE DESCRIPTION: SEQ ID NO:49:

AGCTTAACCT AATTCTAACA AGCAAAGATG TTATTC                                      36

(2) INFORMATION FOR SEQ ID NO:50:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..35
        (D) OTHER INFORMATION: /function= "oligonucleotide 50"

(xi) SEQUENCE DESCRIPTION: SEQ ID NO:50:

TAAGAATAAC ATCTTTGCTT GTTAGAATTA GGTTA                                       35

```
(2) INFORMATION FOR SEQ ID NO:51:

(i) SEQUENCE CHARACTERISTICS:
        (A) LENGTH: 11 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..11
        (D) OTHER INFORMATION: /function= "oligonucleotide 51"

(xi) SEQUENCE DESCRIPTION: SEQ ID NO:51:

ATCTGAATAA A                                                           11

(2) INFORMATION FOR SEQ ID NO:52:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..15
        (D) OTHER INFORMATION: /function= "oligonucleotide 52"

(xi) SEQUENCE DESCRIPTION: SEQ ID NO:52:

AGCTTTTATT CAGAT                                                       15

(2) INFORMATION FOR SEQ ID NO:53:

(i) SEQUENCE CHARACTERISTICS:
        (A) LENGTH: 31 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..31
        (D) OTHER INFORMATION: /function= "oligonucleotide 58"

(xi) SEQUENCE DESCRIPTION: SEQ ID NO:53:

CGCCAATAAA AAAACAAGCT TAACCTAATT C                                     31

(2) INFORMATION FOR SEQ ID NO:54:

(i) SEQUENCE CHARACTERISTICS:
        (A) LENGTH: 46 base pairs
        (B) TYPE: nucleic acid
        (C) STRANDEDNESS: double
        (D) TOPOLOGY: linear
```

(ii) MOLECULE TYPE: cDNA (iii) HYPOTHETICAL: NO (iv) ANTI-SENSE: NO (ix) FEATURE:
           (A) NAME/KEY: misc_feature
           (B) LOCATION: 1..46
           (D) OTHER INFORMATION: /function= "oligonucleotide 59"

(xi) SEQUENCE DESCRIPTION: SEQ ID NO:54:

CGCCAATAAA AAAACAAACT AAACCTAATT CTAACAAGCA AAGATG                     46

(2) INFORMATION FOR SEQ ID NO:55:

(i) SEQUENCE CHARACTERISTICS:
          (A) LENGTH: 46 base pairs
          (B) TYPE: nucleic acid
          (C) STRANDEDNESS: double
          (D) TOPOLOGY: linear (ii) MOLECULE TYPE: cDNA (iii) HYPOTHETICAL: NO (iv) ANTI-SENSE: NO (ix) FEATURE:
          (A) NAME/KEY: misc_feature
          (B) LOCATION: 1..46
          (D) OTHER INFORMATION: /function= "oligonucleotide 60"

(xi) SEQUENCE DESCRIPTION: SEQ ID NO:55:

CGCCAATAAA AAAACAAGCT TAACCTAATT CTAACAAGCA AAGATG                     46

(2) INFORMATION FOR SEQ ID NO:56:

(i) SEQUENCE CHARACTERISTICS:
          (A) LENGTH: 40 base pairs
          (B) TYPE: nucleic acid
          (C) STRANDEDNESS: double
          (D) TOPOLOGY: linear (ii) MOLECULE TYPE: cDNA (iii) HYPOTHETICAL: NO (iv) ANTI-SENSE: NO (ix) FEATURE:
          (A) NAME/KEY: misc_feature
          (B) LOCATION: 1..40
          (D) OTHER INFORMATION: /function= "oligonucleotide 61"

(xi) SEQUENCE DESCRIPTION: SEQ ID NO:56:

AGCTTAACCT AATTCTAACA AGCAAAGATG GGTCCAATTG                            40

(2) INFORMATION FOR SEQ ID NO:57:

(i) SEQUENCE CHARACTERISTICS:
          (A) LENGTH: 40 base pairs
          (B) TYPE: nucleic acid
          (C) STRANDEDNESS: double
          (D) TOPOLOGY: linear (ii) MOLECULE TYPE: cDNA (iii) HYPOTHETICAL: NO (iv) ANTI-SENSE: NO

```
    (ix) FEATURE:
         (A) NAME/KEY: misc_feature
         (B) LOCATION: 1..40
         (D) OTHER INFORMATION: /function= "oligonucleotide 62"

(xi) SEQUENCE DESCRIPTION: SEQ ID NO:57:

TCGACAATTG GACCCATCTT TGCTTGTTAG AATTAGGTTA                              40

(2) INFORMATION FOR SEQ ID NO:58:

(i) SEQUENCE CHARACTERISTICS:
         (A) LENGTH: 56 base pairs
         (B) TYPE: nucleic acid
         (C) STRANDEDNESS: double
         (D) TOPOLOGY: linear (ii) MOLECULE TYPE: cDNA (iii) HYPOTHETICAL: NO (iv) ANTI-SENSE: NO (ix) FEATURE:
         (A) NAME/KEY: misc_feature
         (B) LOCATION: 1..56
         (D) OTHER INFORMATION: /function= "oligonucleotide 63"

(xi) SEQUENCE DESCRIPTION: SEQ ID NO:58:

CGTTGGTGTT GCTAACGGTG CTGGTGTTAG AACTACTGCT TTATTAACTG ATTAAA           56

(2) INFORMATION FOR SEQ ID NO:59:

(i) SEQUENCE CHARACTERISTICS:
         (A) LENGTH: 62 base pairs
         (B) TYPE: nucleic acid
         (C) STRANDEDNESS: double
         (D) TOPOLOGY: linear (ii) MOLECULE TYPE: cDNA (iii) HYPOTHETICAL: NO (iv) ANTI-SENSE: NO (ix) FEATURE:
         (A) NAME/KEY: misc_feature
         (B) LOCATION: 1..62
         (D) OTHER INFORMATION: /function= "oligonucleotide 64"

(xi) SEQUENCE DESCRIPTION: SEQ ID NO:59:

AGCTTTTAAT CAGTTAATAA AGCAGTAGTT CTAACACCAG CACCGTTAGC AACACCAACG        60

AT                                                                      62

(2) INFORMATION FOR SEQ ID NO:60:

(i) SEQUENCE CHARACTERISTICS:
         (A) LENGTH: 14 base pairs
         (B) TYPE: nucleic acid
         (C) STRANDEDNESS: double
         (D) TOPOLOGY: linear (ii) MOLECULE TYPE: cDNA (iii) HYPOTHETICAL: NO (iv) ANTI-SENSE: NO (ix) FEATURE:
         (A) NAME/KEY: misc_feature
         (B) LOCATION: 1..14
         (D) OTHER INFORMATION: /function= "SEQ 70"
```

(xi) SEQUENCE DESCRIPTION: SEQ ID NO:60:

GTNGAYAARC AYWS                                                          14

(2) INFORMATION FOR SEQ ID NO:61:

(i) SEQUENCE CHARACTERISTICS:
         (A) LENGTH: 14 base pairs
         (B) TYPE: nucleic acid
         (C) STRANDEDNESS: double
         (D) TOPOLOGY: linear (ii) MOLECULE TYPE: cDNA (iii) HYPOTHETICAL: NO (iv) ANTI-SENSE: NO (ix) FEATURE:
         (A) NAME/KEY: misc_feature
         (B) LOCATION: 1..14
         (D) OTHER INFORMATION: /function= "SEQ 71"

(xi) SEQUENCE DESCRIPTION: SEQ ID NO:61:

SWRTGYTTRT CNAC                                                          14

(2) INFORMATION FOR SEQ ID NO:62:

(i) SEQUENCE CHARACTERISTICS:
         (A) LENGTH: 14 base pairs
         (B) TYPE: nucleic acid
         (C) STRANDEDNESS: double
         (D) TOPOLOGY: linear (ii) MOLECULE TYPE: cDNA (iii) HYPOTHETICAL: NO (iv) ANTI-SENSE: NO (ix) FEATURE:
         (A) NAME/KEY: misc_feature
         (B) LOCATION: 1..14
         (D) OTHER INFORMATION: /function= "SEQ 72"

(xi) SEQUENCE DESCRIPTION: SEQ ID NO:62:

CCNATGATHW SNGG                                                          14

(2) INFORMATION FOR SEQ ID NO:63:

(i) SEQUENCE CHARACTERISTICS:
         (A) LENGTH: 14 base pairs
         (B) TYPE: nucleic acid
         (C) STRANDEDNESS: double
         (D) TOPOLOGY: linear (ii) MOLECULE TYPE: cDNA (iii) HYPOTHETICAL: NO (iv) ANTI-SENSE: NO (ix) FEATURE:
         (A) NAME/KEY: misc_feature
         (B) LOCATION: 1..14
         (D) OTHER INFORMATION: /function= "SEQ 73"

(xi) SEQUENCE DESCRIPTION: SEQ ID NO:63:

CCNSWDATCA TNGG                                                          14

(2) INFORMATION FOR SEQ ID NO:64:

```
    (i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..14
        (D) OTHER INFORMATION: /function= "SEQ 74"

(xi) SEQUENCE DESCRIPTION: SEQ ID NO:64:

MGNGAYATHA CNGC                                                      14

(2) INFORMATION FOR SEQ ID NO:65:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..14
        (D) OTHER INFORMATION: /function= "SEQ 75"

(xi) SEQUENCE DESCRIPTION: SEQ ID NO:65:

GCNGTDATRT CNCK                                                      14

(2) INFORMATION FOR SEQ ID NO:66:

(i) SEQUENCE CHARACTERISTICS:
        (A) LENGTH: 1311 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: 1..1311
        (D) OTHER INFORMATION: /function= "Figure 4"

(ix) FEATURE:
        (A) NAME/KEY: CDS
        (B) LOCATION: 2..1311

(xi) SEQUENCE DESCRIPTION: SEQ ID NO:66:

C TTA GCT CAA GAA ATT ATT AGA AAA AAA AGA GAT GGT CAT GCT TTA         46
  Leu Ala Gln Glu Ile Ile Arg Lys Lys Arg Asp Gly His Ala Leu
  1               5                   10                  15

TCT GAT GAA GAA ATT AGA TTC TTC ATT AAC GGT ATT AGA GAT AAC ACT       94
Ser Asp Glu Glu Ile Arg Phe Phe Ile Asn Gly Ile Arg Asp Asn Thr
                20                  25                  30
```

-continued

| | |
|---|---|
| ATT TCT GAA GGT CAA ATT GCT GCT TTA GCT ATG ACT ATT TTC TTC CAT<br>Ile Ser Glu Gly Gln Ile Ala Ala Leu Ala Met Thr Ile Phe Phe His<br>35                             40                            45 | 142 |
| GAT ATG ACT ATG CCA GAA AGA GTT TCT TTA ACT ATG GCT ATG AGA GAT<br>Asp Met Thr Met Pro Glu Arg Val Ser Leu Thr Met Ala Met Arg Asp<br>     50                         55                        60 | 190 |
| TCT GGT ACT GTT TTA GAT TGG AAA TCT TTA CAT TTA AAC GGT CCA ATT<br>Ser Gly Thr Val Leu Asp Trp Lys Ser Leu His Leu Asn Gly Pro Ile<br>65                             70                          75 | 238 |
| GTC GAC AAA CAT TCT ACT GGT GGT GTT GGT GAT GTT ACT TCT TTA ATG<br>Val Asp Lys His Ser Thr Gly Gly Val Gly Asp Val Thr Ser Leu Met<br>80                             85                        90                        95 | 286 |
| TTA GGT CCA ATG GTT GCT GCT TGT GGT GGT TAC ATT CCA ATG ATT TCT<br>Leu Gly Pro Met Val Ala Ala Cys Gly Gly Tyr Ile Pro Met Ile Ser<br>              100                        105                       110 | 334 |
| GGT AGA GGT TTA GGT CAT ACT GGT GGT ACT TTA GAT AAA TTA GAA TCT<br>Gly Arg Gly Leu Gly His Thr Gly Gly Thr Leu Asp Lys Leu Glu Ser<br>              115                        120                       125 | 382 |
| ATT CCA GGT TTC GAT ATT TTC CCA GAT GAT AAC AGA TTC AGA GAA ATT<br>Ile Pro Gly Phe Asp Ile Phe Pro Asp Asp Asn Arg Phe Arg Glu Ile<br>              130                        135                       140 | 430 |
| ATT AAA GAT GTT GGT GTT GCT ATT ATT GGT CAA ACT TCT TCT TTA GCT<br>Ile Lys Asp Val Gly Val Ala Ile Ile Gly Gln Thr Ser Ser Leu Ala<br>145                           150                        155 | 478 |
| CCA GCT GAT AAA AGA TTC TAC GCT ACT AGA GAT ATT ACT GCT ACT GTT<br>Pro Ala Asp Lys Arg Phe Tyr Ala Thr Arg Asp Ile Thr Ala Thr Val<br>160                           165                        170                       175 | 526 |
| GAT TCT ATT CCA TTA ATT ACT GCT TCT ATT TTA GCT AAA AAA TTA GCT<br>Asp Ser Ile Pro Leu Ile Thr Ala Ser Ile Leu Ala Lys Lys Leu Ala<br>              180                        185                       190 | 574 |
| GAA GGT TTA GAT GCT TTA GTT ATG GAT GTT AAA GTT GGT TCT GGT GCT<br>Glu Gly Leu Asp Ala Leu Val Met Asp Val Lys Val Gly Ser Gly Ala<br>              195                        200                       205 | 622 |
| TTC ATG CCA ACT TAC GAA TTA TCT GAA GCC TTG GCT GAA GCG ATC GTT<br>Phe Met Pro Thr Tyr Glu Leu Ser Glu Ala Leu Ala Glu Ala Ile Val<br>              210                        215                       220 | 670 |
| GGT GTT GCT AAC GGT GCT GGT GTT AGA ACT ACT GCT TTA TTA ACT GAT<br>Gly Val Ala Asn Gly Ala Gly Val Arg Thr Thr Ala Leu Leu Thr Asp<br>225                           230                        235 | 718 |
| ATG AAC CAA GTT TTA GCT TCT TCT GCT GGT AAC GCT GTT GAA GTT AGA<br>Met Asn Gln Val Leu Ala Ser Ser Ala Gly Asn Ala Val Glu Val Arg<br>240                         245                        250                       255 | 766 |
| GAA GCT GTT CAA TTC TTA ACT GGT GAA TAC AGA AAC CCA AGA TTA TTC<br>Glu Ala Val Gln Phe Leu Thr Gly Glu Tyr Arg Asn Pro Arg Leu Phe<br>              260                        265                       270 | 814 |
| GAT GTT ACT ATG GCT TTA TGT GTT GAA ATG TTA ATT TCT GGT AAA TTA<br>Asp Val Thr Met Ala Leu Cys Val Glu Met Leu Ile Ser Gly Lys Leu<br>              275                        280                       285 | 862 |
| GCT AAA GAT GAT GCT GAA GCT AGA GCT AAA TTA CAA GCT GTT TTA GAT<br>Ala Lys Asp Asp Ala Glu Ala Arg Ala Lys Leu Gln Ala Val Leu Asp<br>290                           295                        300 | 910 |
| AAC GGT AAA GCT GCT GAA GTT TTC GGT AGA ATG GTT GCT GCT CAA AAA<br>Asn Gly Lys Ala Ala Glu Val Phe Gly Arg Met Val Ala Ala Gln Lys<br>305                           310                        315 | 958 |
| GGT CCA ACT GAT TTC GTT GAA AAC TAC GCT AAA TAC TTA CCA ACT GCT<br>Gly Pro Thr Asp Phe Val Glu Asn Tyr Ala Lys Tyr Leu Pro Thr Ala<br>320                           325                        330                       335 | 1006 |
| ATG TTA ACT AAA GCT GTT TAC GCT GAT ACT GAA GGT TTC GTT TCT GAA<br>Met Leu Thr Lys Ala Val Tyr Ala Asp Thr Glu Gly Phe Val Ser Glu<br>              340                        345                       350 | 1054 |

```
ATG GAT ACT AGA GCT TTA GGT ATG GCT GTT GTT GCT ATG GGT GGT GGT     1102
Met Asp Thr Arg Ala Leu Gly Met Ala Val Val Ala Met Gly Gly Gly
            355                 360                 365

AGA AGA CAA GCC TCT GAT ACT ATT GAT TAC TCT GTT GGT TTC ACT GAT     1150
Arg Arg Gln Ala Ser Asp Thr Ile Asp Tyr Ser Val Gly Phe Thr Asp
        370                 375                 380

ATG GCT AGA TTA GGT GAT CAA GTT GAT GGT CAA AGA CCA TTA GCT GTT     1198
Met Ala Arg Leu Gly Asp Gln Val Asp Gly Gln Arg Pro Leu Ala Val
    385                 390                 395

ATT CAT GCT AAA GAT GAA AAC AAC TGG CAA GAA GCT GCT AAA GCT GTT     1246
Ile His Ala Lys Asp Glu Asn Asn Trp Gln Glu Ala Ala Lys Ala Val
400                 405                 410                 415

AAA GCT GCT ATT AAA TTA GCT GAT AAA GCT CCA GAA TCT ACT CCA ACT     1294
Lys Ala Ala Ile Lys Leu Ala Asp Lys Ala Pro Glu Ser Thr Pro Thr
                420                 425                 430

GTT TAC AGA AGG ATA TC                                              1311
Val Tyr Arg Arg Ile
            435
```

(2) INFORMATION FOR SEQ ID NO:67:

(i) SEQUENCE CHARACTERISTICS:
        (A) LENGTH: 436 amino acids
        (B) TYPE: amino acid
        (D) TOPOLOGY: linear (ii) MOLECULE TYPE: protein (xi) SEQUENCE DESCRIPTION: SEQ ID NO:67:

```
Leu Ala Gln Glu Ile Ile Arg Lys Lys Arg Asp Gly His Ala Leu Ser
 1               5                  10                  15

Asp Glu Glu Ile Arg Phe Phe Ile Asn Gly Ile Arg Asp Asn Thr Ile
            20                  25                  30

Ser Glu Gly Gln Ile Ala Ala Leu Ala Met Thr Ile Phe Phe His Asp
        35                  40                  45

Met Thr Met Pro Glu Arg Val Ser Leu Thr Met Ala Met Arg Asp Ser
    50                  55                  60

Gly Thr Val Leu Asp Trp Lys Ser Leu His Leu Asn Gly Pro Ile Val
65                  70                  75                  80

Asp Lys His Ser Thr Gly Gly Val Gly Asp Val Thr Ser Leu Met Leu
                85                  90                  95

Gly Pro Met Val Ala Ala Cys Gly Gly Tyr Ile Pro Met Ile Ser Gly
            100                 105                 110

Arg Gly Leu Gly His Thr Gly Thr Leu Asp Lys Leu Glu Ser Ile
        115                 120                 125

Pro Gly Phe Asp Ile Phe Pro Asp Asp Asn Arg Phe Arg Glu Ile Ile
    130                 135                 140

Lys Asp Val Gly Val Ala Ile Ile Gly Gln Thr Ser Ser Leu Ala Pro
145                 150                 155                 160

Ala Asp Lys Arg Phe Tyr Ala Thr Arg Asp Ile Thr Ala Thr Val Asp
                165                 170                 175

Ser Ile Pro Leu Ile Thr Ala Ser Ile Leu Ala Lys Lys Leu Ala Glu
            180                 185                 190

Gly Leu Asp Ala Leu Val Met Asp Val Lys Val Gly Ser Gly Ala Phe
        195                 200                 205

Met Pro Thr Tyr Glu Leu Ser Glu Ala Leu Ala Glu Ala Ile Val Gly
    210                 215                 220
```

```
Val Ala Asn Gly Ala Gly Val Arg Thr Thr Ala Leu Leu Thr Asp Met
225                 230                 235                 240

Asn Gln Val Leu Ala Ser Ser Ala Gly Asn Ala Val Glu Val Arg Glu
            245                 250                 255

Ala Val Gln Phe Leu Thr Gly Glu Tyr Arg Asn Pro Arg Leu Phe Asp
            260                 265                 270

Val Thr Met Ala Leu Cys Val Glu Met Leu Ile Ser Gly Lys Leu Ala
            275                 280                 285

Lys Asp Asp Ala Glu Ala Arg Ala Lys Leu Gln Ala Val Leu Asp Asn
290                 295                 300

Gly Lys Ala Ala Glu Val Phe Gly Arg Met Val Ala Ala Gln Lys Gly
305                 310                 315                 320

Pro Thr Asp Phe Val Glu Asn Tyr Ala Lys Tyr Leu Pro Thr Ala Met
                325                 330                 335

Leu Thr Lys Ala Val Tyr Ala Asp Thr Glu Gly Phe Val Ser Glu Met
                340                 345                 350

Asp Thr Arg Ala Leu Gly Met Ala Val Val Ala Met Gly Gly Gly Arg
                355                 360                 365

Arg Gln Ala Ser Asp Thr Ile Asp Tyr Ser Val Gly Phe Thr Asp Met
370                 375                 380

Ala Arg Leu Gly Asp Gln Val Asp Gly Gln Arg Pro Leu Ala Val Ile
385                 390                 395                 400

His Ala Lys Asp Glu Asn Asn Trp Gln Glu Ala Ala Lys Ala Val Lys
                405                 410                 415

Ala Ala Ile Lys Leu Ala Asp Lys Ala Pro Glu Ser Thr Pro Thr Val
                420                 425                 430

Tyr Arg Arg Ile
        435

(2) INFORMATION FOR SEQ ID NO:68:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: 1..33
        (D) OTHER INFORMATION: /function= "Fig.18 - region 82-92"

(ix) FEATURE:
        (A) NAME/KEY: CDS
        (B) LOCATION: 1..33

(xi) SEQUENCE DESCRIPTION: SEQ ID NO:68:

GTNGAYAARC AYWSNACNGG NGGNGTNGGN GAY                              33

(2) INFORMATION FOR SEQ ID NO:69:

(i) SEQUENCE CHARACTERISTICS:
        (A) LENGTH: 11 amino acids
        (B) TYPE: amino acid
        (C) STRANDEDNESS: single
        (D) TOPOLOGY: linear
```

```
        (ii) MOLECULE TYPE: peptide (ix) FEATURE:
             (A) NAME/KEY: Region
             (B) LOCATION: 1..11
             (D) OTHER INFORMATION: /note= "Fig.18 - Amino acid
                 sequence encoded by region 82-92"

(xi) SEQUENCE DESCRIPTION: SEQ ID NO:69:

Val Asp Lys His Ser Thr Gly Gly Val Gly Asp
1               5                   10

(2) INFORMATION FOR SEQ ID NO:70:

(i) SEQUENCE CHARACTERISTICS:
             (A) LENGTH: 72 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: NO (ix) FEATURE:
             (A) NAME/KEY: misc_feature
             (B) LOCATION: 1..72
             (D) OTHER INFORMATION: /function= "Fig.18 - region
                 110-133"

(ix) FEATURE:
             (A) NAME/KEY: CDS
             (B) LOCATION: 1..72

(xi) SEQUENCE DESCRIPTION: SEQ ID NO:70:

CCNATGATHW SNGGNMGNGG NYTNGGNCAY ACNGGNGGNA CNYTNGAYAA RYTNGARWSN        60

ATHCCNGGNT TY                                                          72

(2) INFORMATION FOR SEQ ID NO:71:

(i) SEQUENCE CHARACTERISTICS:
             (A) LENGTH: 24 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Region
             (B) LOCATION: 1..24
             (D) OTHER INFORMATION: /note= "Fig.18 - amino acid
                 sequence encoded by region 110-133"

(xi) SEQUENCE DESCRIPTION: SEQ ID NO:71:

Pro Met Ile Ser Gly Arg Gly Leu Gly His Thr Gly Gly Thr Leu Asp
1               5                   10                  15

Lys Leu Glu Ser Ile Pro Gly Phe
            20

(2) INFORMATION FOR SEQ ID NO:72:

(i) SEQUENCE CHARACTERISTICS:
             (A) LENGTH: 78 base pairs
             (B) TYPE: nucleic acid
             (C) STRANDEDNESS: double
             (D) TOPOLOGY: linear (ii) MOLECULE TYPE: DNA (genomic)
```

```
        (iii) HYPOTHETICAL: NO (iv) ANTI-SENSE: NO (ix) FEATURE:
             (A) NAME/KEY: misc_feature
             (B) LOCATION: 1..78
             (D) OTHER INFORMATION: /function= "Fig.18 - region
                 171-196"

(ix) FEATURE:
             (A) NAME/KEY: CDS
             (B) LOCATION: 1..78

(xi) SEQUENCE DESCRIPTION: SEQ ID NO:72:

MGNGAYATHA CNGCNACNGT NGAYWSNATH CCNYTNATHA CNGCNWSNAT HYTNGCNAAR       60

AARYTNGCNG ARGGNYTN                                                    78

(2) INFORMATION FOR SEQ ID NO:73:

(i) SEQUENCE CHARACTERISTICS:
             (A) LENGTH: 26 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Region
             (B) LOCATION: 1..26
             (D) OTHER INFORMATION: /note= "Fig.18 - amino acid
                 sequence encoded by region 171-196"

(xi) SEQUENCE DESCRIPTION: SEQ ID NO:73:

Arg Asp Ile Thr Ala Thr Val Asp Ser Ile Pro Leu Ile Thr Ala Ser
1               5                   10                  15

Ile Leu Ala Lys Lys Leu Ala Glu Gly Leu
            20                  25

(2) INFORMATION FOR SEQ ID NO:74:

(i) SEQUENCE CHARACTERISTICS:
             (A) LENGTH: 33 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: YES (ix) FEATURE:
             (A) NAME/KEY: misc_feature
             (B) LOCATION: 1..33
             (D) OTHER INFORMATION: /function= "Fig.18 - anti-sense to
                 region 82-92"

(xi) SEQUENCE DESCRIPTION: SEQ ID NO:74:

RTCNCCNACN CCNCCNGTNS WRTGYTTRTC NAC                                   33

(2) INFORMATION FOR SEQ ID NO:75:

(i) SEQUENCE CHARACTERISTICS:
             (A) LENGTH: 72 base pairs
             (B) TYPE: nucleic acid
             (C) STRANDEDNESS: double
             (D) TOPOLOGY: linear
```

(ii) MOLECULE TYPE: DNA (genomic)

(iii) HYPOTHETICAL: NO (iv) ANTI-SENSE: YES (ix) FEATURE:
            (A) NAME/KEY: misc_feature
            (B) LOCATION: 1..72
            (D) OTHER INFORMATION: /function= "Fig.18 - anti-sense to
                region 110-133"

(xi) SEQUENCE DESCRIPTION: SEQ ID NO:75:

RAANCCNGGD ATNSWYTCNA RYTTRTCNAR NGTNCCNCCN GTRTGNCCNA RNCCNCKNCC          60

NSWDATCATN GG                                                             72

(2) INFORMATION FOR SEQ ID NO:76:

(i) SEQUENCE CHARACTERISTICS:
            (A) LENGTH: 78 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: YES (ix) FEATURE:
            (A) NAME/KEY: misc_feature
            (B) LOCATION: 1..78
            (D) OTHER INFORMATION: /function= "Fig.18 - anti-sense to
                region 171-196"

(xi) SEQUENCE DESCRIPTION: SEQ ID NO:76:

NARNCCYTCN GCNARYTTYT TNGCNARDAT NSWNGCNGTD ATNARNGGDA TNSWRTCNAC          60

NGTNGCNGTD ATRTCNCK                                                       78